US008719054B2

(12) United States Patent  
Jung et al.

(10) Patent No.: US 8,719,054 B2
(45) Date of Patent: *May 6, 2014

(54) ENHANCED COMMUNICATION LINK FOR PATIENT DIAGNOSIS AND TREATMENT

(75) Inventors: Edward K. Y. Jung, Bellevue, WA (US); Royce A. Levien, Lexington, MA (US); Robert W. Lord, Seattle, WA (US); Mark A. Malamud, Seattle, WA (US); John D. Rinaldo, Jr., Bellevue, WA (US); Lowell L. Wood, Jr., Livermore, CA (US)

(73) Assignee: The Invention Science Fund I, LLC, Bellevue, WA (US)

(*) Notice: Subject to any disclaimer, the term of this patent is extended or adjusted under 35 U.S.C. 154(b) by 1681 days.

This patent is subject to a terminal disclaimer.

(21) Appl. No.: 11/588,116

(22) Filed: Oct. 25, 2006

(65) Prior Publication Data

US 2008/0000996 A1    Jan. 3, 2008

Related U.S. Application Data

(63) Continuation-in-part of application No. 11/489,244, filed on Jul. 18, 2006, which is a continuation-in-part of application No. 11/478,569, filed on Jun. 29, 2006.

(51) Int. Cl.
*A61B 5/00* (2006.01)
*G06F 19/00* (2011.01)

(52) U.S. Cl.
USPC .......................................................... 705/3

(58) Field of Classification Search
USPC .......................................................... 705/2, 3
See application file for complete search history.

(56) References Cited

U.S. PATENT DOCUMENTS

| | | |
|---|---|---|
| 3,970,996 A | 7/1976 | Yasaka et al. |
| 4,156,620 A | 5/1979 | Clemens |
| 4,164,320 A | 8/1979 | Irazoqui et al. |
| 4,695,954 A | 9/1987 | Rose et al. |
| 4,781,704 A | 11/1988 | Potter |
| 4,843,377 A | 6/1989 | Fuller et al. |
| 4,857,713 A | 8/1989 | Brown et al. |
| 4,857,716 A | 8/1989 | Gombrich et al. |
| 4,930,997 A | 6/1990 | Bennett |
| 4,999,613 A | 3/1991 | Williamson et al. |
| 5,026,084 A | 6/1991 | Pasfield |
| 5,092,850 A | 3/1992 | Buma |
| 5,236,432 A * | 8/1993 | Matsen et al. ............. 606/88 |
| 5,947,937 A | 9/1999 | Urrutia et al. |
| 6,024,699 A | 2/2000 | Surwit et al. |
| 6,294,999 B1 | 9/2001 | Yarin et al. |
| 6,380,858 B1 | 4/2002 | Yarin et al. |
| 6,454,705 B1 | 9/2002 | Cosentino et al. |
| 6,523,009 B1 | 2/2003 | Wilkins |
| 6,575,969 B1 | 6/2003 | Rittman, III et al. |

(Continued)

OTHER PUBLICATIONS

U.S. Appl. No. 11/588,116, Jung et al.

(Continued)

*Primary Examiner* — John Pauls
*Assistant Examiner* — Trang Nguyen

(57) ABSTRACT

Exemplary embodiments provide a verification technique that facilitates administration of a health-related procedure to an intended recipient patient or group of patients. An interface template or signal protocol may be configured to establish suitable matching between the patient and various types of objects used to administer the health-related procedure.

19 Claims, 20 Drawing Sheets

(56) References Cited

U.S. PATENT DOCUMENTS

| | | | |
|---|---|---|---|
| 6,671,563 | B1 | 12/2003 | Engelson et al. |
| 6,699,193 | B2* | 3/2004 | Crutchfield et al. .......... 600/454 |
| 6,790,198 | B1 | 9/2004 | White et al. |
| 6,824,052 | B2 | 11/2004 | Walsh |
| 6,980,111 | B2 | 12/2005 | Nolte |
| 7,029,034 | B2 | 4/2006 | Newell |
| 7,039,628 | B2 | 5/2006 | Logan, Jr. |
| 7,321,862 | B2 | 1/2008 | Rosenfeld et al. |
| 7,411,509 | B2 | 8/2008 | Rosenfeld et al. |
| 7,853,455 | B2 | 12/2010 | Brown |
| 2001/0054155 | A1* | 12/2001 | Hagan et al. .................. 713/193 |
| 2002/0016719 | A1 | 2/2002 | Nemeth et al. |
| 2002/0022972 | A1 | 2/2002 | Costello |
| 2002/0032583 | A1 | 3/2002 | Joao |
| 2002/0052763 | A1 | 5/2002 | Jung Richardson |
| 2002/0055858 | A1* | 5/2002 | Jackson ............................ 705/3 |
| 2002/0065686 | A1* | 5/2002 | Monteleone et al. ............. 705/3 |
| 2002/0067270 | A1 | 6/2002 | Yarin et al. |
| 2002/0188259 | A1 | 12/2002 | Hickle et al. |
| 2003/0022141 | A1 | 1/2003 | Packard |
| 2003/0036683 | A1 | 2/2003 | Kehr et al. |
| 2003/0040700 | A1* | 2/2003 | Hickle et al. ..................... 604/67 |
| 2003/0140928 | A1 | 7/2003 | Bui et al. |
| 2003/0208382 | A1 | 11/2003 | Westfall |
| 2003/0212579 | A1 | 11/2003 | Brown et al. |
| 2004/0010425 | A1* | 1/2004 | Wilkes et al. ..................... 705/3 |
| 2004/0026501 | A1 | 2/2004 | Walsh |
| 2004/0045031 | A1* | 3/2004 | Gautier ......................... 725/110 |
| 2004/0203692 | A1 | 10/2004 | Schwinke et al. |
| 2004/0254816 | A1* | 12/2004 | Myers ............................... 705/2 |
| 2005/0060188 | A1 | 3/2005 | Valley |
| 2005/0115561 | A1* | 6/2005 | Stahmann et al. ....... 128/200.24 |
| 2005/0119534 | A1* | 6/2005 | Trost et al. .................... 600/300 |
| 2005/0139651 | A1* | 6/2005 | Lim et al. ....................... 235/380 |
| 2005/0165627 | A1 | 7/2005 | Fotsch et al. |
| 2005/0187789 | A1 | 8/2005 | Hatlestad et al. |
| 2005/0218152 | A1 | 10/2005 | Simon |
| 2005/0240304 | A1 | 10/2005 | York et al. |
| 2005/0251102 | A1* | 11/2005 | Hegland et al. ............... 604/500 |
| 2005/0258244 | A1 | 11/2005 | Mitchell et al. |
| 2006/0028727 | A1 | 2/2006 | Moon et al. |
| 2006/0058917 | A1 | 3/2006 | Vonk et al. |
| 2006/0061472 | A1 | 3/2006 | Lovoi et al. |
| 2006/0064087 | A1 | 3/2006 | Mirza et al. |
| 2006/0097516 | A1 | 5/2006 | Kozlowski et al. |
| 2006/0229918 | A1 | 10/2006 | Fotsch et al. |
| 2006/0265245 | A1* | 11/2006 | McCallie et al. .................. 705/2 |
| 2006/0278222 | A1* | 12/2006 | Schermeier et al. ..... 128/204.18 |
| 2007/0016443 | A1 | 1/2007 | Wachman et al. |
| 2007/0018121 | A1 | 1/2007 | Leyman et al. |
| 2007/0043590 | A1 | 2/2007 | Lee |
| 2007/0061167 | A1 | 3/2007 | Brown |
| 2007/0233854 | A1* | 10/2007 | Bukovec et al. .............. 709/224 |
| 2007/0274574 | A1 | 11/2007 | Boult et al. |

OTHER PUBLICATIONS

U.S. Appl. No. 11/584,812, Jung et al.
U.S. Appl. No. 11/580,692, Jung et al.
U.S. Appl. No. 11/580,525, Jung et al.
U.S. Appl. No. 11/149,464, Jung et al.
"Acquiring, Organizing, and Displaying Medical Information"; Insight: A Tool for Viewing Data, Finding Answers, and Seeing Patterns; bearing a date of 2006; pp. 1-7.
Aller, MD, Raymond; "Positive patient identification: more than a double check"; System Review Series; bearing a date of Oct. 2005; pp. 26-34.
Avery, Catherine; "Quantum Leap in Medical Infornatics"; Washington Hospital Center Physician; vol. 10—No. 10; bearing a date of Dec. 2004-Jan. 2005; pp. 1, 10-11.
Beyea, Suzanne C.; "Patient identification—a crucial aspect of patient safety—Patient Safety First"; AORN Journal; bearing a date of Sep. 2003; pp. 1-3.
Beyea, Suzanne C.; "Systems that reduce the potential for patient identification errors"; AORN Journal; bearing a date of Sep. 2002; pp. 1-4.
"Convergence CT Introduces Inpatient Insight Hospital Patient-Level Data for Pharmaceutical Market Research and Clinical Trial Planning;" San Francisco—(Business Wire)—Nov. 13, 2003; pp. 1; located at http://findarticles.com/p/articles/mi_m0E1N/is_2003_Nov_13/ai_n27 . . . .
"Former head of UHP's DUI unit ends appeal of alcohol-related conviction"; The Salt Lake Tribune; bearing a date of Mar. 3, 2008; pp. 1-2; located at http://www.sltrib.com/fdcp?1204574945509.
Greene, Jay; "Cover Story Essential news and information for physician business executives"; vol. 10/No. 10; bearing a date of Oct. 2006; pp. 1-7.
Holstein, William J.; "Patient Safety Through Technology"; Published Feb. 17, 2007, The New York Times; pp. 1-2.
McCarthy, Carloline; "Microsoft coughs up for health care software"; c/net news.com; bearing a date of Jul. 27, 2006; pp. 1-2; located at http://news.com.com/2102-1014_3-6098696.html?tag=st.util.print.
Microsoft Executive Circle Case Study Detail; "Washington Hospital Center"; bearing a date of Jan. 20, 2004; pp. 1-5; located at http://www.microsoft.com/business/executivecircle/content/casestud . . . .
"PAR3 and Vitality, Inc. Join Forces to Improve Medication Adherence With Combined Solutions"; PAR3 Communications, Inc.; bearing a date of Aug. 28, 2007; pp. 1-2; located at http://www.prnewswire.ca/cgi-bin-stories.pl?ACCT=104&STORY . . . .
"Precision Dynamics' Bar Code System Solutions for Positive Patient Identification Featured at MUSE Conference"; Precision Dynamics Corporation; bearing a date of May 4, 2006; pp. 1-2.
Symbol Technologies, Inc.; "Safer Patient Care: Automated Medication Verification Solutions for Hospitals and Clinics"; bearing a date of 2003; pp. 1-3.
The Whittington Hospital NHS Trust; "Information for Staff to Accompany Patient Identification Policy"; bearing a date of Mar. 2003; pp. 1-14.
Versweyveld, Leslie; "Misys Insight clinical decision support tool integrates data from heterogeneous, enterprise-wide health care systems"; Virtual Medical Worlds Monthly; bearing a date of Jul. 23, 2002; pp. 1-3; located at http://www.hoise.com/vmw/02/articles/vmw/LV-VM-08-02-15.html.
White, Charlie; "Glowcap Ambient Pill Cap"; Bearing a date of May 29, 2007; pp. 1.

* cited by examiner

US 8,719,054 B2

ENHANCED COMMUNICATION LINK FOR PATIENT DIAGNOSIS AND TREATMENT

PRIORITY CLAIM, CROSS-REFERENCE TO RELATED APPLICATION, AND INCORPORATION BY REFERENCE

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation in part of U.S. patent application Ser. No. 11/489,244 entitled ENHANCED COMMUNICATION LINK FOR PATIENT DIAGNOSIS AND TREATMENT, naming Edward K. Y. Jung, Royce A. Levien, Robert W. Lord, Mark A. Malamud, John D. Rinaldo, Jr. and Lowell L. Wood, Jr. as inventors, filed 18 Jul. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/478,569 entitled VERIFICATION TECHNIQUE FOR PATIENT DIAGNOSIS AND TREATMENT, naming Edward K. Y. Jung, Royce A. Levien, Robert W. Lord, Mark A. Malamud, John D. Rinaldo, Jr. and Lowell L. Wood, Jr. as inventors, filed 29 Jun. 2006, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior- Filed Application, USPTO Official Gazette Mar. 18, 2003, available at http://www.uspto.gov/web/offices/com/sol/og/2003/week11/ patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

BACKGROUND

Systems and methods for providing diagnosis, treatment, and other health-related procedures need additional safeguards to help assure proper administration to a designated patient.

SUMMARY

Various embodiments and implementations are disclosed herein with respect to improved systems and methods for administering appropriate health-related procedures to one or more patients.

Some system embodiments for patient verification may include a first version of identification information that serves as an identifier for a health status of at least one particular patient; a second version of the identification information that is associated with a selected procedure intended for the particular patient; and a customized interface signal protocol configured for correlating the first version with the second version of the identification information, which interface signal protocol facilitates suitable matching of the selected procedure with the particular patient.

Other system embodiments for a patient identification system may include a health-related procedure that is intended to be rendered to at least one particular patient; a signal confirmation protocol to facilitate suitable matching of the heal-related procedure with the at least one particular patient; and an interface module associated with the at least one particular patient, which interface module includes primary identification information capable of correlation with complementary secondary identification information associated with the health-related procedure pursuant to signal transmission to or from the interface module.

Additional patient identification system embodiments may include a health-related procedure that is intended to be rendered to one or more patients, one or more product components to be used in connection with the health-related procedure, a communication module incorporated with the one or more product components; and a signal confirmation protocol to facilitate suitable matching of the health-related procedure with the one or more patients. Other system features may include identification information associated with the one or more product components, which identification information is capable of correlation with complementary patient identification information associated with the one or more patients pursuant to signal transmission to or from the communication module.

An exemplary process embodiment for patient verification may include establishing a signal confirmation protocol that includes identification information related to a particular patient, incorporating a first version of the identification information in an interface module associated with the particular patient, incorporating a second version of the identification information in a communication module associated with a selected procedure intended for the particular patient, and implementing the signal confirmation protocol via a communication link between the communication module and the interface module to facilitate suitable matching of the selected procedure with the particular patient.

A further possible system implementation for providing patient identification may include a health-related procedure that is intended to be rendered to a specified group of patients having a same or similar type of health-related issue; one or more product components to be used in connection with the health-related procedure; and identification information associated with at least one of the product components, which identification information is recognizable pursuant to a signal confirmation protocol for suitable matching with complementary patient identification information associated with the specified group of patients.

Yet another exemplary system embodiment for patient identification may include a signal confirmation protocol that includes identification information related to a particular patient; an interface module associated with the particular patient and including a first version of the identification information; a communication module associated with a selected health-related procedure and including a second complementary version of the identification information; and a communication link between the interface module and the communication module for implementing a signal transmission in accordance with the signal confirmation protocol to facilitate suitable matching of the particular patient with the health-related procedure to be rendered to the particular patient.

Various process components may be incorporated in computer program products having instructions encoded on storage or transmission media for executing and implementing the process steps. For example, such a process may include providing a signal confirmation protocol based on identification information related to a particular patient, which identification information includes a first version incorporated in an interface module associated with the particular patient and a second version incorporated in a communication module associated with a selected health-related procedure intended for the particular patient; and activating the signal confirmation protocol via a communication link between the communication module and the interface module to facilitate suitable matching of the selected procedure with the particular patient.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
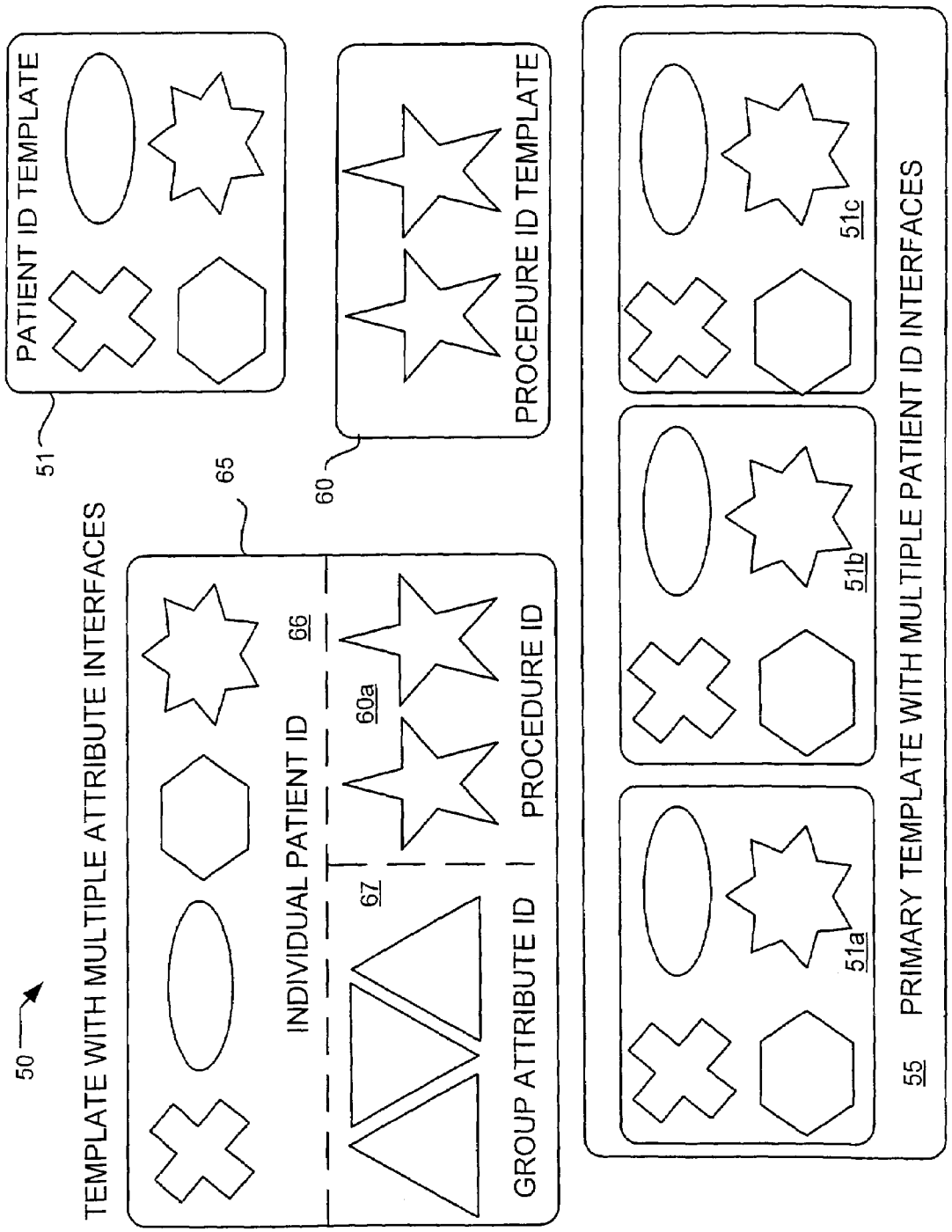
FIG. 1 is a schematic representation of exemplary patient verification features that may be incorporated in an interface template.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The patient identification techniques disclosed herein may be adapted for the administration of many types of health-related procedures. Accordingly it is not possible to recite a complete listing of such health-related procedures that may incorporate the various interface template aspects illustrated in the exemplary disclosed embodiments.

However it may be helpful to understand a recently developed technique for marking medication and other health-related products with a visual identifier that facilitates proper administration of a substance dosage to designated patient. In that regard the. following commonly assigned pending application is incorporated herein by reference: Ser. No. 11/474, 109 entitled "Customized Visual Marking for Medication Labeling", filed 23 Jun. 2006.

It will be further understood that patient identification issues involving administration of health-related procedures affect many types of persons and entities including but not limited to manufacturers, distributors, wholesalers, retailers, hospitals, hospices, convalescent homes, emergency care facilities, pharmacies, health insurance providers, HMOs, clinics, home nursing services, and the like. It is believed that the various aspects and implementations for the patient verification techniques disclosed herein can be adapted for the benefit of such persons and entities as well as for the benefit of their clients and patients.

The exemplary patient verification features 50 shown in FIG. 1 include a patient ID template 51, a primary template 55 with multiple patient ID interfaces, and another template 65 with multiple attribute interfaces. It will be understood that an exemplary template associated with a particular patient may be configured as an interface for verifiable matching engagement with secondary template associated with a health-related procedure.

The patient ID template 51 includes various interface elements (e.g., shown schematically as a four-part configuration) that collectively serve as an identifier for health-related issues involving a particular patient, or in some instances a group of patients. Such a patient interface configuration may be implemented in a primary version of an interface template associated with a particular patient (e.g., attached to a body part, attached to a patient identifier, located proximate to a patient, incorporated with a patient support structure, located remotely from the patient, etc.), and also implemented in a complementary secondary version of the interface template that may be associated with a selected procedure intended for the particular patient or group of patients.

The primary template 55 shows an exemplary implementation of a composite three interface template that may be located in proximity to the particular patient. It will be noted that such a unitary interface template may have practical advantages as compared to using three separate patient ID templates 51. However it will be noted that multiple unitary templates as well as a composite multiple interface template allow for possible simultaneous matching engagement with three different selected patient procedures, and also for matching engagement with secondary procedure ID templates associated with different components of a health-related procedure.

The procedure ID template 60 includes various interface elements (e.g., shown schematically as a twin-type configuration) that collectively serve as an identifier for health-related issues involving a specified type of patient procedure.

The template 65 is shown schematically with an individual patient ID interface 66, a procedure ID interface 60*a*, and a group attribute ID interface 67. The individual patient ID interface 66 includes a different layout of the four-part configuration shown in patient ID template 51, but both interface configurations 51, 66 may serve as an identifier for the same particular patient. It will be noted that the procedure ID interface 60*a* incorporates the same twin-type configuration as shown in procedure ID template 60 in order for both interface configurations of 60, 60*a* to serve as an identifier for the same health-related procedure.

The triplet-type interface configuration shown in group attribute ID 67 provides capability for a template configuration to serve as an identifier of several patients that share a health-related relationship or affiliation.

It will be understood from the illustrated embodiments disclosed herein that some implementations may provide a patient identifier attachable to a bodily part of the particular patient, which patient identifier includes or is physically coupled to the interface template. In some instances the patient identifier may be attachable to a support structure for the particular patient, which patient identifier includes or is physically coupled to the interface template.

Further possible embodiments may provide an interface template in proximity to the particular patient, or provide an interface template located remotely from the particular patient. Other possible implementations may provide a plurality of interface templates including a first attribute interface serving as an identifier of the particular patient and a second attribute interface serving as an identifier of the health-related procedure. Such interface templates may be complementary to matching interface template configurations associated with a particular health-related procedure.

Some embodiments may provide a plurality of complementary interface templates that include a first attribute interface serving as an identifier of the particular patient and a second attribute interface serving as an identifier of a group of patients having a same or similar type of health-related issue. Other possible system features may include a plurality of complementary interface templates having two or more attribute interfaces each serving as an identifier of the particular patient to enable verifiable matching engagement with multiple complementary interface templates associated with a health-related procedure.

Some embodiments may further provide a computer program product including instructions encoded on storage or transmission media, which instructions implement a process for verification of the matching engagement between the interface template associated with the particular patient and the complementary interface template associated with a health-related procedure to be rendered to the particular patient.

Additional embodiments may provide a computer program product including instructions encoded on storage or transmission media, which instructions implement a process for providing a status indication regarding whether the matching engagement has occurred between the interface template associated with the particular patient and the complementary interface template associated with a health-related procedure to be rendered to the particular patient.

Further possible embodiments may provide a computer program product including instructions encoded on storage or transmission media, which instructions implement a process for preventing activation of the health-related procedure in the absence of satisfactory matching engagement between the interface template associated with the particular patient and the complementary interface template associated with a health-related procedure to be rendered to the particular patient.

Figure 2:
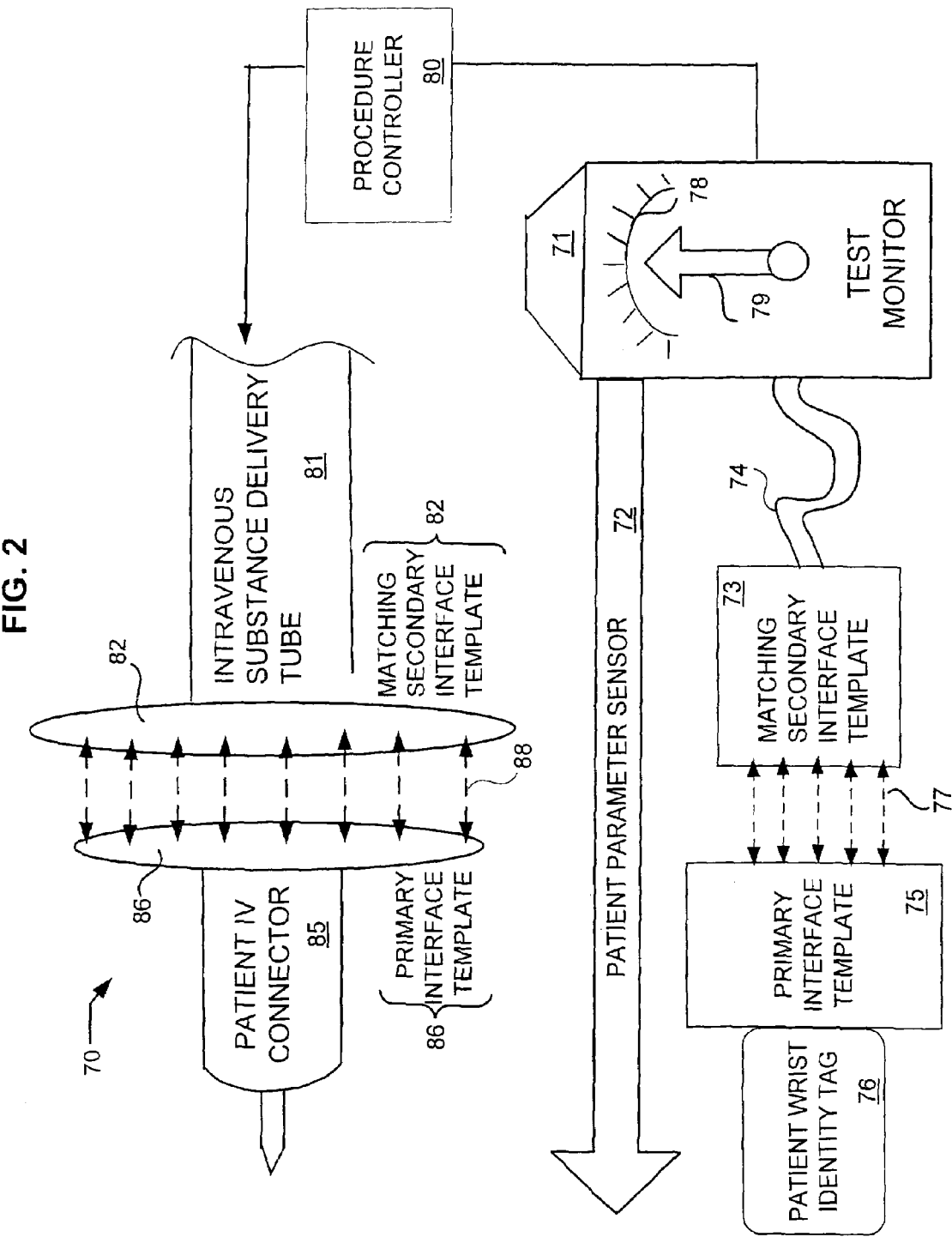
FIG. 2 is a schematic representation of exemplary embodiments that may be implemented in connection with a health-related procedure

The exemplary embodiments 70 of FIG. 2 disclose test monitor 71, patient parameter sensor 72, connector link 74, and procedure controller 80 operably coupled with intravenous substance delivery tube 81. A designated patient who is an intended recipient of the intravenous administration procedures may have a patient wrist identity tag 76 integral with or attachable to a primary interface template 75, and may also have a patient IV connector 85 integral with or attachable to primary interface template 86. The delivery of a health-related substance dosage to the designated patient via the intravenous substance delivery tube 81 may be coordinated by procedure controller 80 with output results generated by test monitor 71. The test monitor 71 may include an indicator arrow 79 that moves along a readout scale 78 to indicate an output result received from the patient parameter sensor 72.

The primary interface templates 75, 86 directly associated with the designated patient may be incorporated in a composite unit (e.g., see primary template 55 in FIG. 1), or may be incorporated in separate units (e.g., see patient ID template 51 in FIG. 1).

It will be noted that an implementation feature of the exemplary embodiments 70 includes a provision for both intravenous procedure components 71, 81 to have separate patient verification interconnections, respectively. Verification for usage of the test monitor 71 with the designated patient is accomplished by correlated interface engagement 77 between primary interface template 75 and matching secondary interface template 73. Verification for usage of the intravenous substance delivery tube 81 with such designated patient is accomplished by correlated interface engagement 88 between primary interface template 86 and matching secondary interface template 82.

Of course it will be understood that in some circumstances a health-related procedure may be configured to have a single patient verification interconnection linked to two or more components used to administer the procedure. In that regard the exemplary embodiments disclosed herein are for purposes of illustration only and are not intended to be limiting.

A substance administration device may be used in connection with administration of the selected procedure, wherein the secondary version of the interface template is associated with the substance administration device.

It will be understood from the various disclosures herein that an exemplary system embodiment may provide the secondary version of the interface template as an integral part of the substance administration device. A further implementation feature may provide a separate product component not integral with the substance administration device, wherein the separate product component includes the secondary version of the interface template as an integral part.

Some embodiments may include a status indicator that is operably coupled to the primary version or the secondary version of the interface template, wherein the status indicator confirms the satisfactory matching engagement between the primary and secondary versions of the interface template. A further system feature may include a control module operably coupled with the substance administration device to prevent activation of the substance administration device in the event there is no verifiable matching engagement between the primary and secondary versions of the interface template. In some instances the control module may be operably coupled with the substance administration device to allow activation of the substance administration device in the event there is confirmation of matching engagement between the primary and secondary versions of the interface template.

It will be understood that various features disclosed herein may be implemented with a diagnostic or testing or treatment device used in connection with administration of the selected health-related procedure, wherein the secondary version of the interface template is associated with such diagnostic or testing or treatment device.

Another exemplary implementation embodiment may include a health-related procedure that involves multiple components which may individually or collectively be integrated with or associated with the secondary version of the interface template.

Further exemplary implementations embodiments may include a patient identification system involving a health-related procedure for administering or dispensing substance dosages of various medications, dietary supplements, test fluids, anesthetics, treatment remedies, etc. (a complete listing is not reasonably possible). The related components used with such a procedure may be integrated with or associated with a complementary secondary version of the interface template.

Other implementations may provide a patient data record used in connection with administration of the selected health-related procedure, wherein the secondary version of the interface template is associated with the patient data record. In some instances a control module may include an access protocol to prevent read access to the patient data record in the event there is no verifiable matching engagement between the primary and secondary versions of the interface template. A further possible system feature may provide a control module that includes an access protocol to prevent write access to the patient data record in the event there is no verifiable matching engagement between the primary and secondary versions of the interface template.

Other possible data record aspects may include a control module having an access protocol to allow read access to the patient data record in the event there is confirmation of matching engagement between the primary and secondary versions of the interface template. Such access protocol may include one or more of the following type of output read access to the patient data record: hardcopy view, hardcopy printout, display monitor, remote access, text access, audio access, image access, fax access, hyperlinked access, and cross-reference link.

Another possible data record aspect may include a control module having an access protocol to allow write access to the patient data record in the event there is confirmation of matching engagement between the primary and secondary versions of the interface template. Such access protocol may allow one or more of the following type of input write access to the patient data record in the event there is confirmation of matching engagement between the primary and secondary versions of the interface template: handwritten, keyboarded, scanned, oral, faxed, remote transmittal, wireless transmittal, data modification, data deletion, hyperlinked data entry, and cross-reference link.

Figure 3:
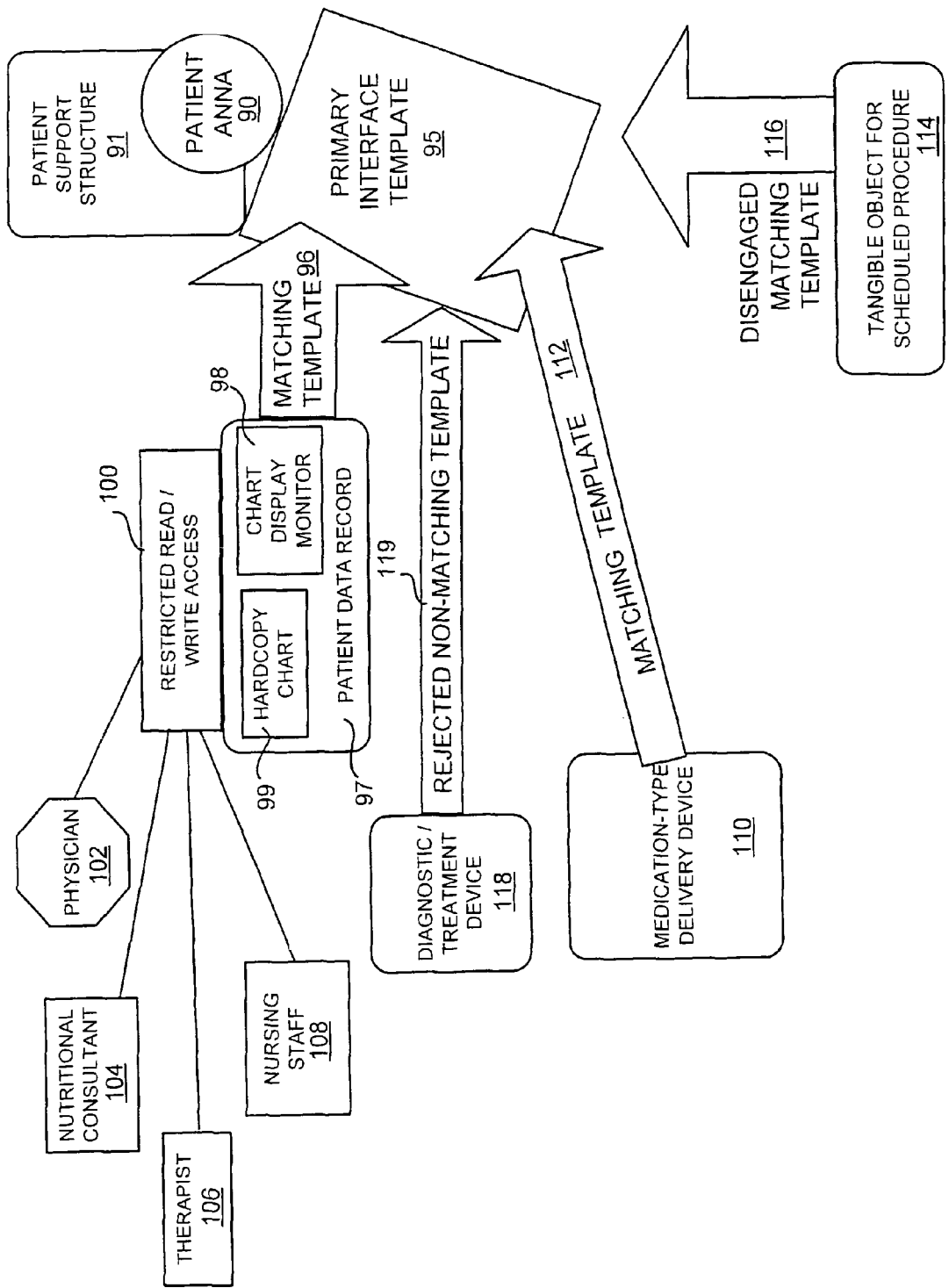
FIG. 3 is a schematic system diagram that illustrates various exemplary patient verification features.

Referring to the exemplary embodiments of FIG. 3, a patient Anna 90 may be temporarily or semi-permanently located with a patient support structure 91 (e.g., chair, bed, gurney, operating table, etc.). One or more primary interface templates 95 may be situated in proximity with patient Anna and/or in close proximity with her patient support structure 91.

It will be understood that health-related procedures can be administered to patient Anna 90 during confinement at a temporary care facility as well as during her daily life activities at a residence, home, work location, or traveling from one place to another. In that regard the exemplary patient verification arrangements disclosed herein are adaptable for use in many different types of patient environments.

An exemplary health-related procedure may include maintenance of a patient data record 97 that may be accessible to patient Anna 90 as well as to other authorized parties such as physician 102, nutritional consultant 104, therapist 106, and nursing staff 108. In order to help assure an acceptable assurance of data integrity, the patient data record 97 may include a restricted read/write access module 100. In some instances a verifiable engagement between Anna's primary interface template 95 and a matching template 96 associated with Anna's patient data record 97 may be required in order before allowing any "read" access (e.g., using hardcopy chart 99 or chart display monitor 98, etc.) or before allowing any "write" access (e.g., handwritten entry, keyboarded entry, scanned entry, etc.) to such patient data record 97.

An exemplary illustrated depiction in FIG. 3 shows the matching template 96 successfully linked together with primary interface template 95 based on a correlated interface engagement.

Other exemplary health-related procedures disclosed in the embodiments of FIG. 3 may involve the use of a medication-type delivery device 110, a tangible object for scheduled procedure 114, and a diagnostic/treatment device 118. Of course it will be understood that many other health-related procedures may also incorporate the patient verification techniques and features disclosed herein.

A further exemplary illustrated depiction in FIG. 3 shows the matching template 112 associated with medication-type deliver device 110 successfully linked together with primary interface template 95 based on a correlated interface engagement. It is noted that successful linkage involving primary patient interface templates may in some instances occur concurrently with multiple secondary interface templates (e.g., see templates 96, 112) associated with different health-related procedures.

Another exemplary illustrated depiction in FIG. 3 shows disengaged matching template 116 associated with tangible object for scheduled procedure 114 awaiting successful linkage with primary interface template 95.

An additional illustrated depiction in FIG. 3 shows an unsuccessful link attempted between non-matching template 119 that is associated with diagnostic/treatment device 118 and the primary interface template 95 that is associated with patient Anna 90.

Various implementation features may include providing an interface template associated with the particular patient, which interface template includes a customized interface configuration shaped for verifiable matching engagement with a complementary interface template associated with the health-related procedure. Some embodiments may provide one or more-complementary interface templates associated with the health-related procedure. Some system features may provide multiple complementary interface templates that are each associated with a different product component, respectively. Another possible feature may provide one interface template associated with multiple product components.

Figure 4:
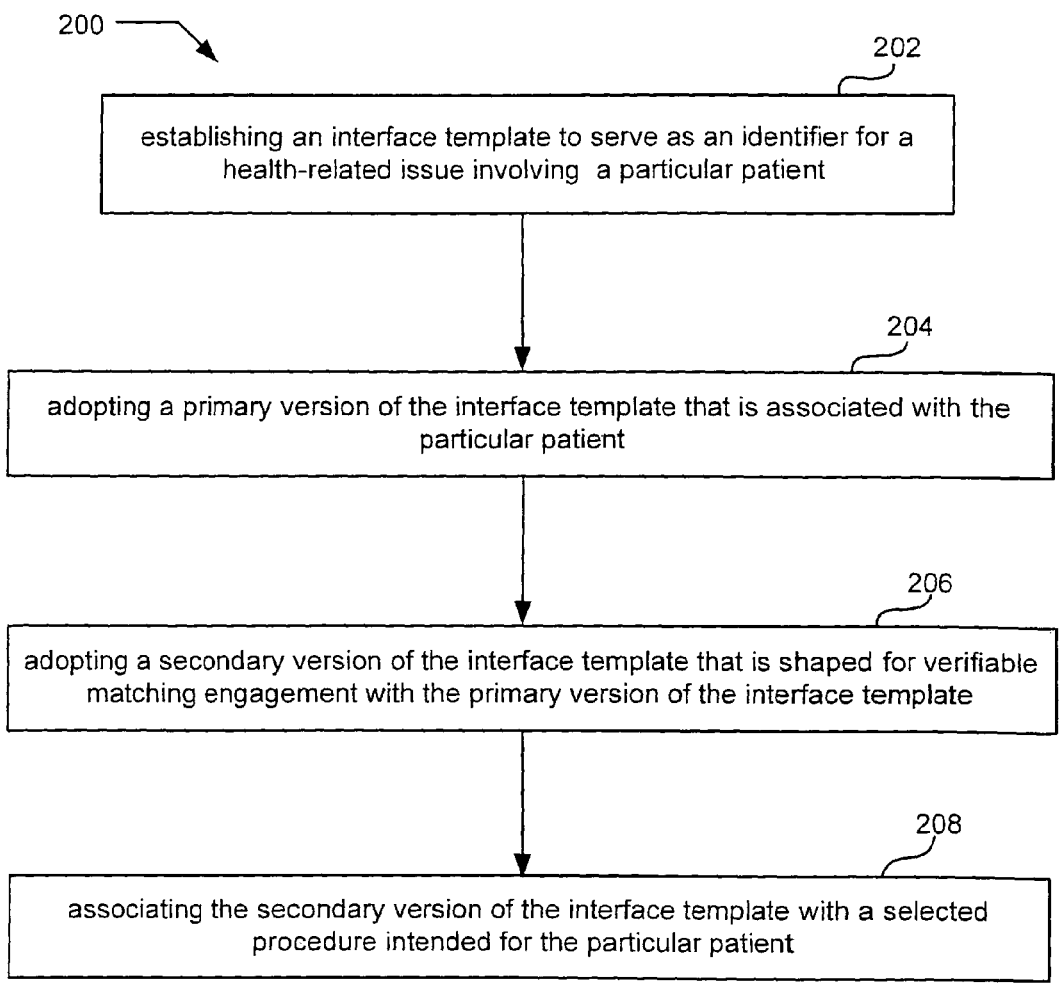
FIG. 4 is a high level flow chart for an exemplary process embodiment.

Referring to the high level flow chart of FIG. 4, an exemplary process embodiment 200 for patient verification includes establishing an interface template to serve as an identifier for a health-related issue involving a particular patient (block 202), adopting a primary version of the interface template that is associated with the particular patient (block 204), adopting a secondary version of the interface template that is shaped for verifiable matching engagement with the primary version of the interface template (block 206), and associating the secondary version of the interface template with a selected procedure intended for the particular patient (block 208).

Figure 5:
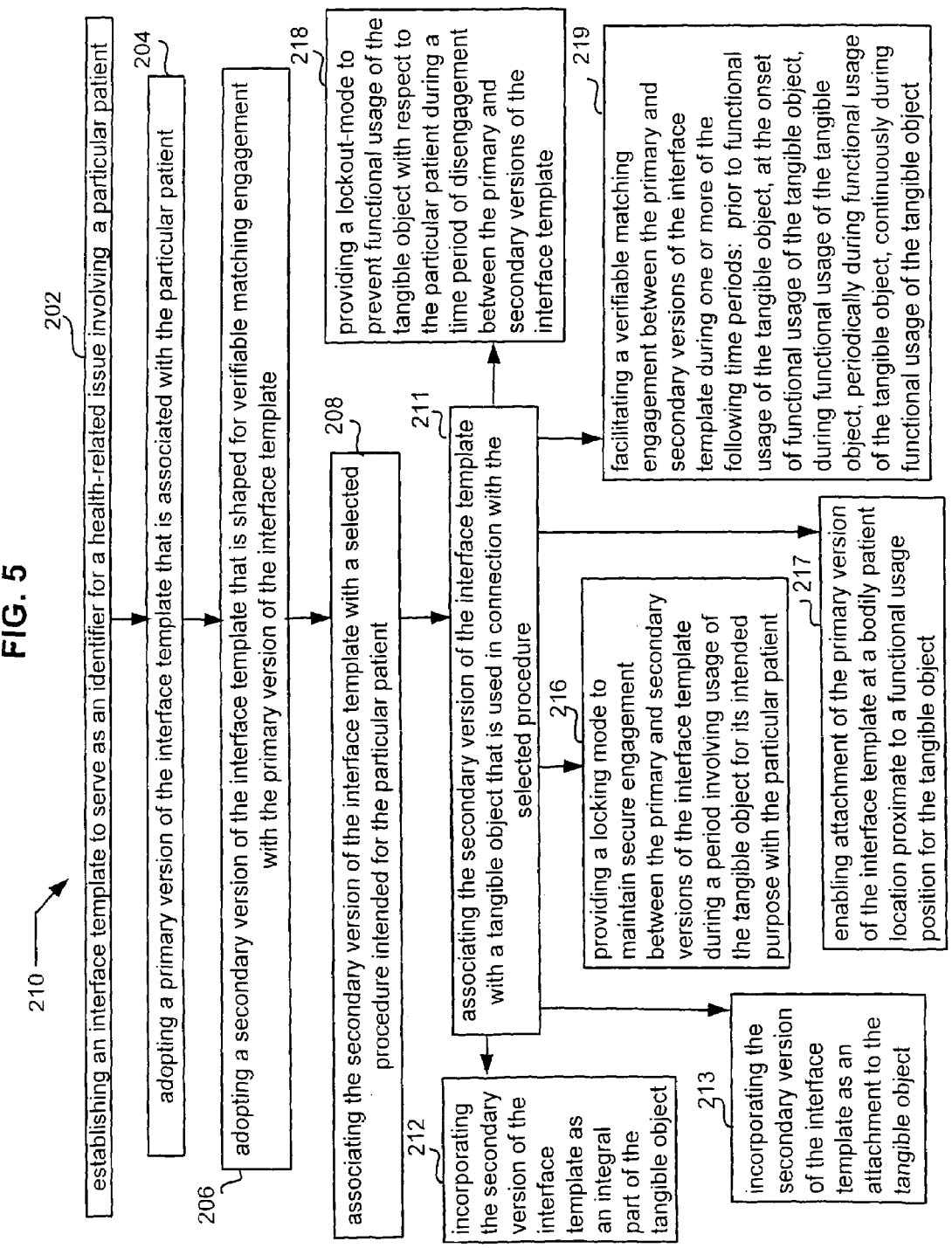
FIGS. 5-8 are flow charts showing more detailed aspects of various exemplary process embodiments.

The additional exemplary embodiment features 210 of FIG. 5 may include previously described process components 202, 204, 206, 208 in combination with associating the secondary version of the interface template with a tangible object that is used in connection with the selected procedure (block 211). Additional possible aspects may include incorporating the secondary version of the interface template as an integral part of the tangible object (block 212), and incorporating the secondary version of the interface template as an attachment to the tangible object (block 213).

Further possible features may include providing a locking mode to maintain secure engagement between the primary and secondary versions of the interface template during a period involving usage of the tangible object for its intended purpose with the particular patient (block 216), and enabling attachment of the primary version of the interface template at a bodily patient location proximate to a functional usage position for the tangible object (block 217).

FIG. 5 also discloses additional exemplary features including providing a lockout-mode to prevent functional usage of the tangible object with respect to the particular patient during a time period of disengagement between the primary and secondary versions of the interface template (block 218), and facilitating a verifiable matching engagement between the primary and secondary versions of the interface template during one or more of the following time periods: prior to functional usage of the tangible object, at the onset of functional usage of the tangible object, during functional usage of the tangible object, periodically during functional usage of the tangible object, continuously during functional usage of the tangible object (block 219).

Figure 6:
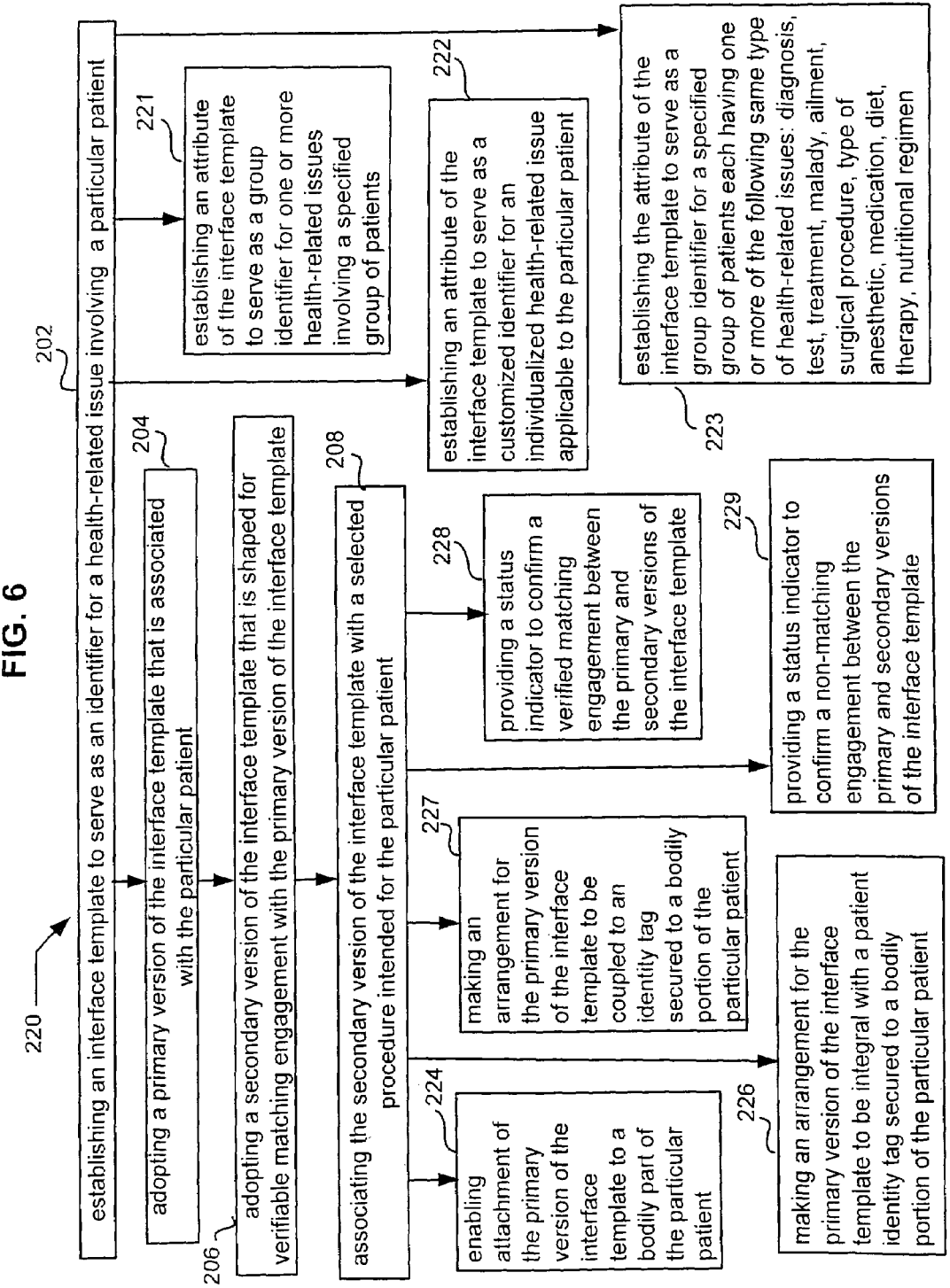

Referring to the exemplary embodiments 220 of FIG. 6, previously disclosed process components 202, 204, 206, 208 may be combined with other features relating to the primary version of the interface template. For example, possible aspects may include enabling attachment of the primary version of the interface template to a bodily part of the particular patient (block 224), making an arrangement for the primary version of the interface template to be integral with a patient identity tag secured to a bodily portion of the particular patient (block 226), and making an arrangement for the primary version of the interface template to be coupled to an identity tag secured to a bodily portion of the particular patient (block 227).

Other exemplary features may include providing a status indicator with an "ok" type of alert to indicate a verified matching engagement between the primary and secondary versions of the interface template (block 228), and providing a status indicator with a "warning" type of alert to indicate a non-matching engagement between the primary and secondary versions of the interface template (block 229).

Further possible implementation features shown in FIG. 6 may include establishing an attribute of the interface template to serve as a group identifier for one or more health-related issues involving a specified group of patients, (block 221), and establishing the attribute of the interface template to serve as a group identifier for a specified group of patients each having one or more of the following same type of health-related issues: diagnosis, test, treatment, malady, ailment, surgical procedure, type of anesthetic, medication, diet, therapy, and nutritional regimen (block 223).

Another exemplary aspect may include establishing an attribute of the interface template to serve as a customized identifier for an individualized health-related issue applicable to the particular patient (block 222).

Figure 7:
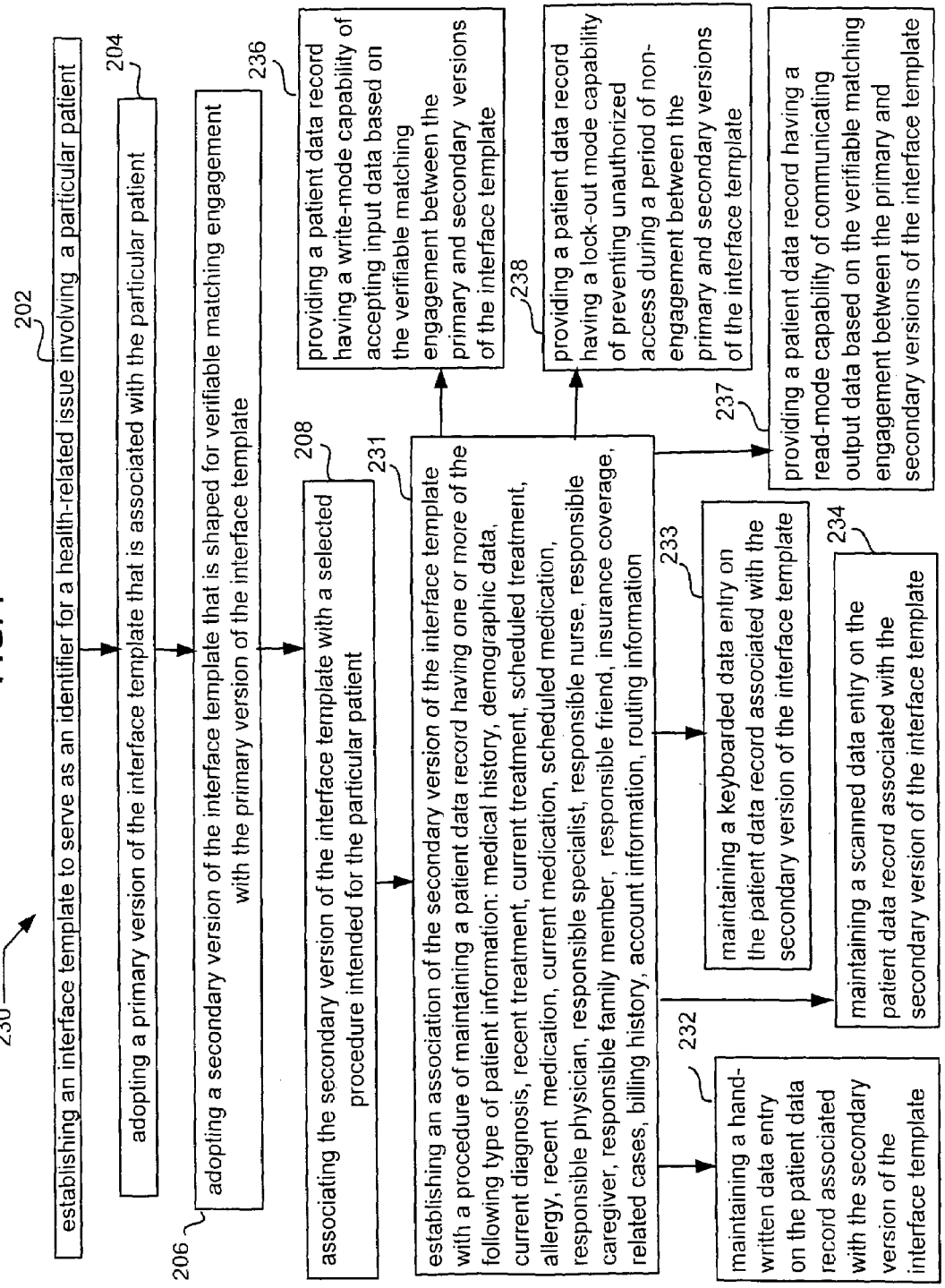

The exemplary process embodiments 230 shown in FIG. 7 may include previously described components 202, 204, 206, 208 along with establishing an association of the secondary version of the interface template with a procedure of maintaining a patient data record having one or more of the following type of patient information: medical history, demographic data, current diagnosis, recent treatment, current treatment, scheduled treatment, allergy, recent medication, current medication, scheduled medication, responsible physician, responsible specialist, responsible nurse, responsible caregiver, responsible family member, responsible friend, insurance coverage, related cases, billing history, account information, and routing information (block 231).

Further illustrated aspects that are possible include maintaining various types of data entries on the patient data record associated with the secondary version of the interface template, including a hand-written data entry (block 232), a keyboarded data entry (block 233), and a scanned data entry (block 234).

Further possible implementation features regarding the patient data record may include providing a patient data record having a write-mode capability of accepting input data based on the verifiable matching engagement between the primary and secondary versions of the interface template (block 236), and providing a patient data record having a read-mode capability of communicating output data based on the verifiable matching engagement between the primary and secondary versions of the interface template (block 237).

Another possible implementation feature may include providing a patient data record having a lock-out mode capability of preventing unauthorized access during a period of non-engagement between the primary and secondary versions of the interface template (block 238).

Figure 8:
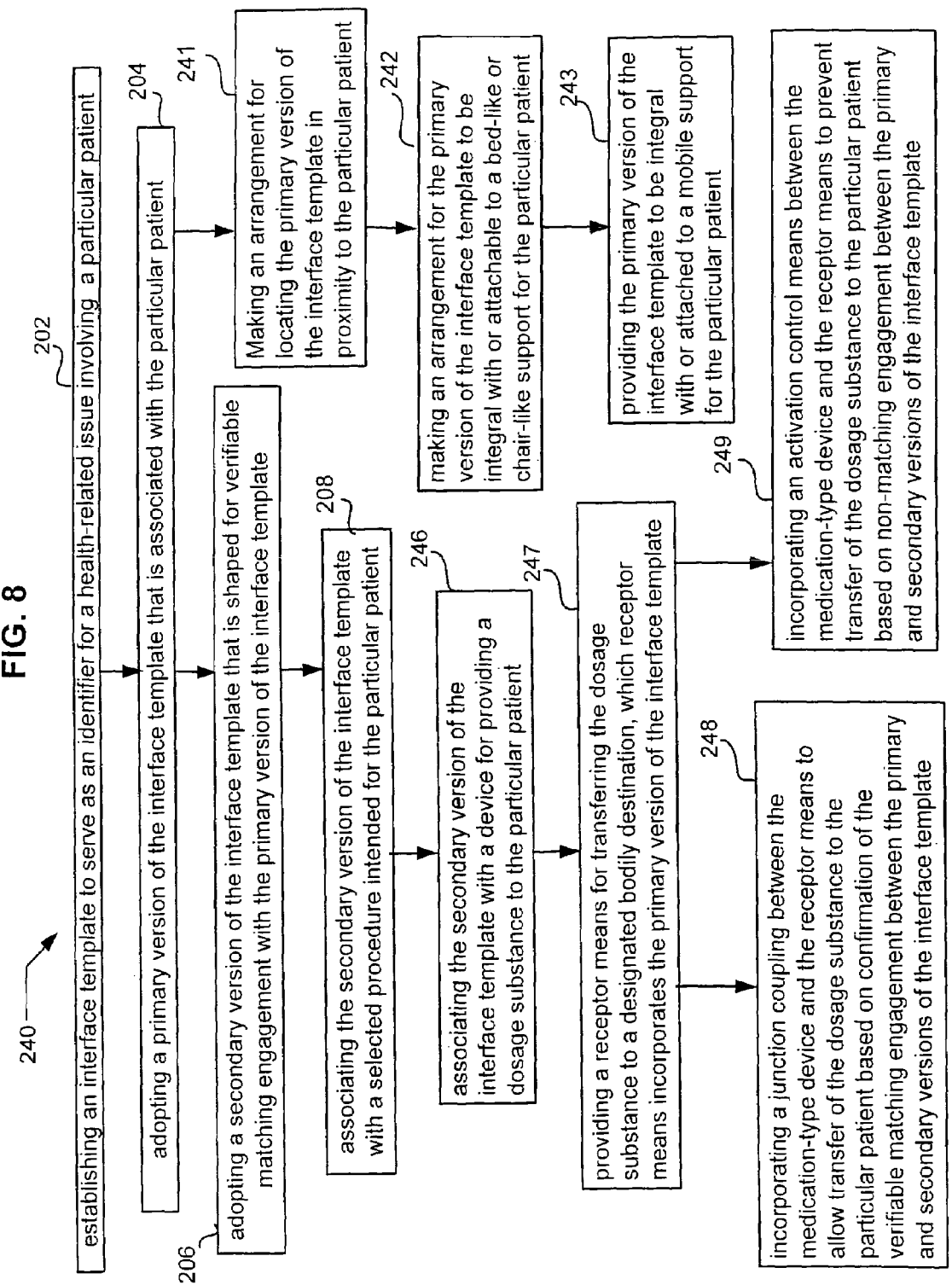

The detailed exemplary embodiment features 240 illustrated in FIG. 8 include previously described process components 202, 204, 206, 208 in combination with making an arrangement for locating the primary version of the interface template in proximity to the particular patient (block 241). Other possible aspects may include making an arrangement for the primary version of the interface template to be integral with or attachable to a bed-like or chair-like support for the particular patient (block 242). In some instances an exemplary embodiment feature may include providing the primary version of the interface template to be integral with or attached to a mobile support for the particular patient (block 243).

Other possible aspects shown in FIG. 8 include associating the secondary version of the interface template with a device for providing a dosage substance to the particular patient (block 246), providing a receptor means for transferring the dosage substance to a designated bodily destination, which receptor means incorporates the primary version of the interface template (block 247), and incorporating a junction coupling between the medication-type device and the receptor means to allow transfer of the dosage substance to the particular patient based on confirmation of the verifiable matching engagement between the primary and secondary versions of the interface template (block 248).

A further exemplary aspect may include incorporating an activation control means between the medication-type device and the receptor means to prevent transfer of the dosage substance to the particular patient based on non-matching engagement between the primary and secondary versions of the interface template (block 249).

Figure 9:
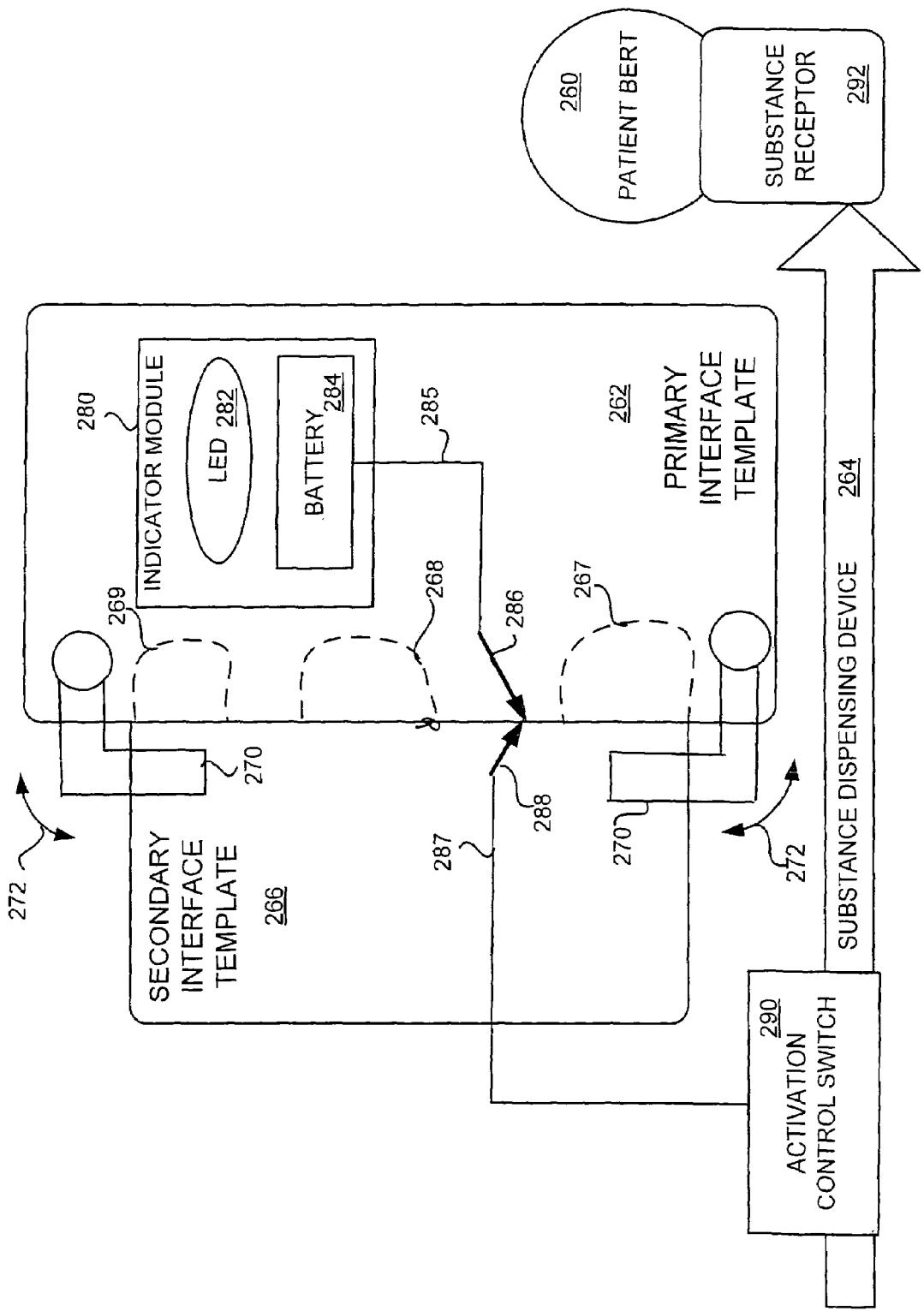
FIG. 9 is a schematic block diagram showing additional interface template embodiments.

The schematic block diagram of FIG. 9 illustrates an exemplary embodiment of a primary interface template 262 associated with patient Bert 260, and a matching secondary interface template 266 associated with substance dispensing device 264. The primary interface template 262 may include an indicator module 280 having a power source such as battery 284 and a status indicator such as light emitting diode (LED) 282. The primary interface template may also include a latching device such as pivotally mounted arms 270 that move back and forth (see arrows 272) between an unlatched position (with the primary interface template 262 and secondary interface template 266 disengaged—not shown) to a latched position with the primary interface template 262 and secondary interface template 266 in verifiable matching engagement (shown in FIG. 9).

Numerous types of matching interface shapes (e.g., pattern, projection, recess, matrix, contour, etc.) are possible for implementing a satisfactory matching engagement. In that regard, the illustrated version of the secondary interface template includes exemplary protrusions 267, 268, 269 (shown in phantom) that are shaped to form a customized pattern matching a complementary corresponding pattern (not shown) on the primary interface template 262.

A signal status line 285 connects battery 284 with a first conductive contact 286 on a surface portion of primary interface template 262. When full matching interface engagement occurs, a second conductive contact 288 is brought into adjacent relationship with the first conductive contact 286 to provide a closed circuit connection that establishes verification of a predetermined correct match-up between the substance dispensing device 264 and the intended recipient patient (or group of patients). Such verification may be confirmed by illumination of LED 282. Alternatively non-illumination of LED 282 is an indicator of non-engagement with the primary interface template 262.

Other functional consequences of such verified engagement may include a data entry provided to a patient data record (see patient data record 97 on FIG. 3), and transmission of a template engagement signal via status line 287 to activation control switch 290. Responsive to such template engagement signal, the activation control switch 290 serves as a junction coupling to enable delivery of a substance dosage via the substance dispensing device 264 to a substance receptor 292 for patient Bert 260. In the absence of such a template engagement signal, the activation control switch 290 remains closed to prevent delivery of any dosage through the substance dispensing device 264.

It will be understood that system embodiment features disclosed herein may be used with product components that include a device for dispensing a substance dosage for external administration to the particular patient, which device is associated with the interface template. In some instances the product components may include a device for dispensing a substance dosage for internal administration to the particular patient, which device is associated with the interface template.

Some embodiments may be implemented in a patient identification system for health-related procedures intended to be rendered to a specified group of patients having a same or similar type of health-related issue. An exemplary interface template may be associated with one or more product components, which interface template includes a customized interface configuration shaped for verifiable matching engagement with a complementary interface template associated with one or more of the patients in the specified group.

A possible group patient implementation aspect may provide a complementary interface template having a first attribute interface that includes a individualized ID configuration to serve as a customized identifier for a particular patient in the specified group, and also having a second attribute interface that includes a generic-type ID configuration to serve as an identifier for the specified group.

Another possible group aspect may provide a system having a complementary interface template that includes an attribute interface configuration to serve as an identifier associated with the health-related procedure.

Figure 10:
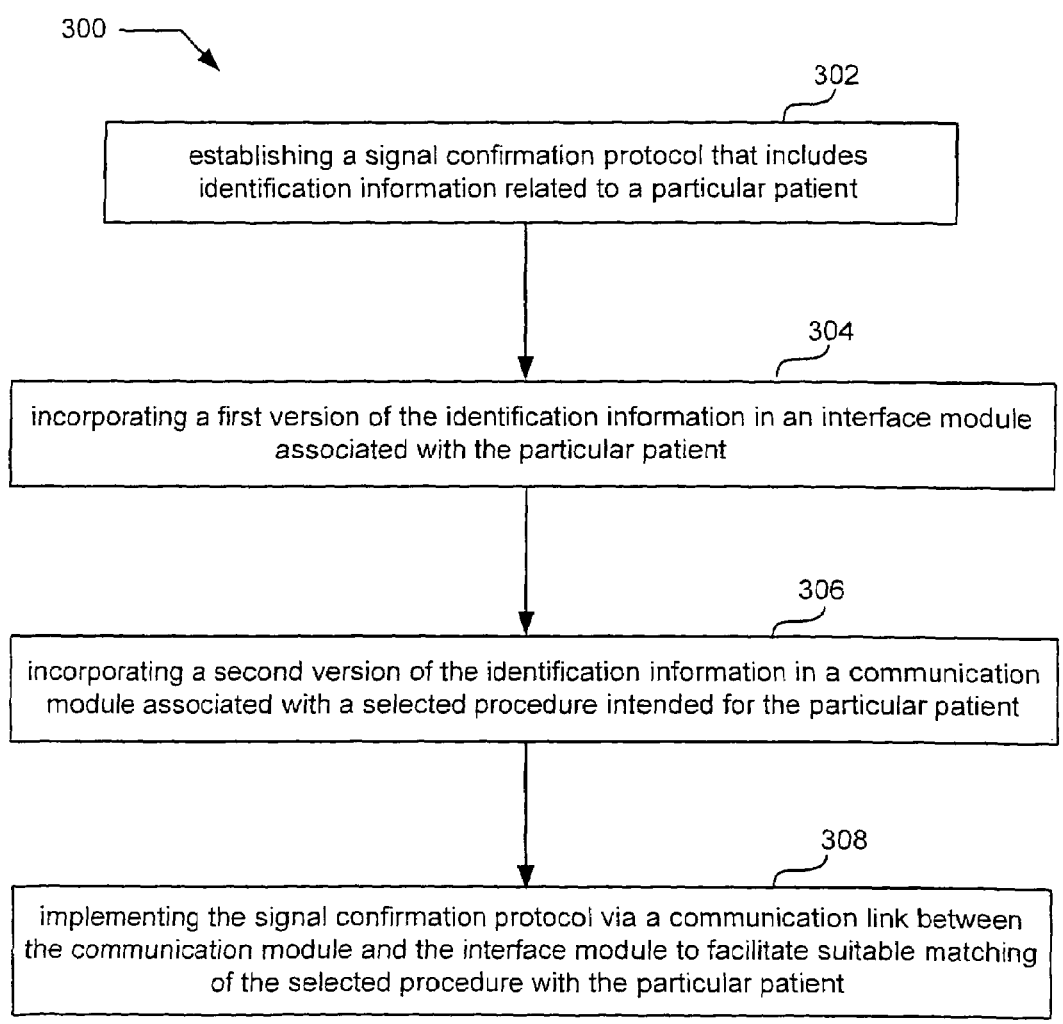
FIG. 10 is a high level flow chart for another exemplary process embodiment.

Referring to an exemplary embodiment 300 for a patient verification process shown in FIG. 10, possible components may include establishing a signal confirmation protocol that includes identification information related to a particular patient (block 302); incorporating a first version of the identification information in an interface module associated with the particular patient (block 304); incorporating a second version of the identification information in a communication module associated with a selected procedure intended for the particular patient (block 306); and implementing the signal confirmation protocol via a communication link between the communication module and the interface module to facilitate suitable matching of the selected procedure with the particular patient (block 308).

Figure 11:
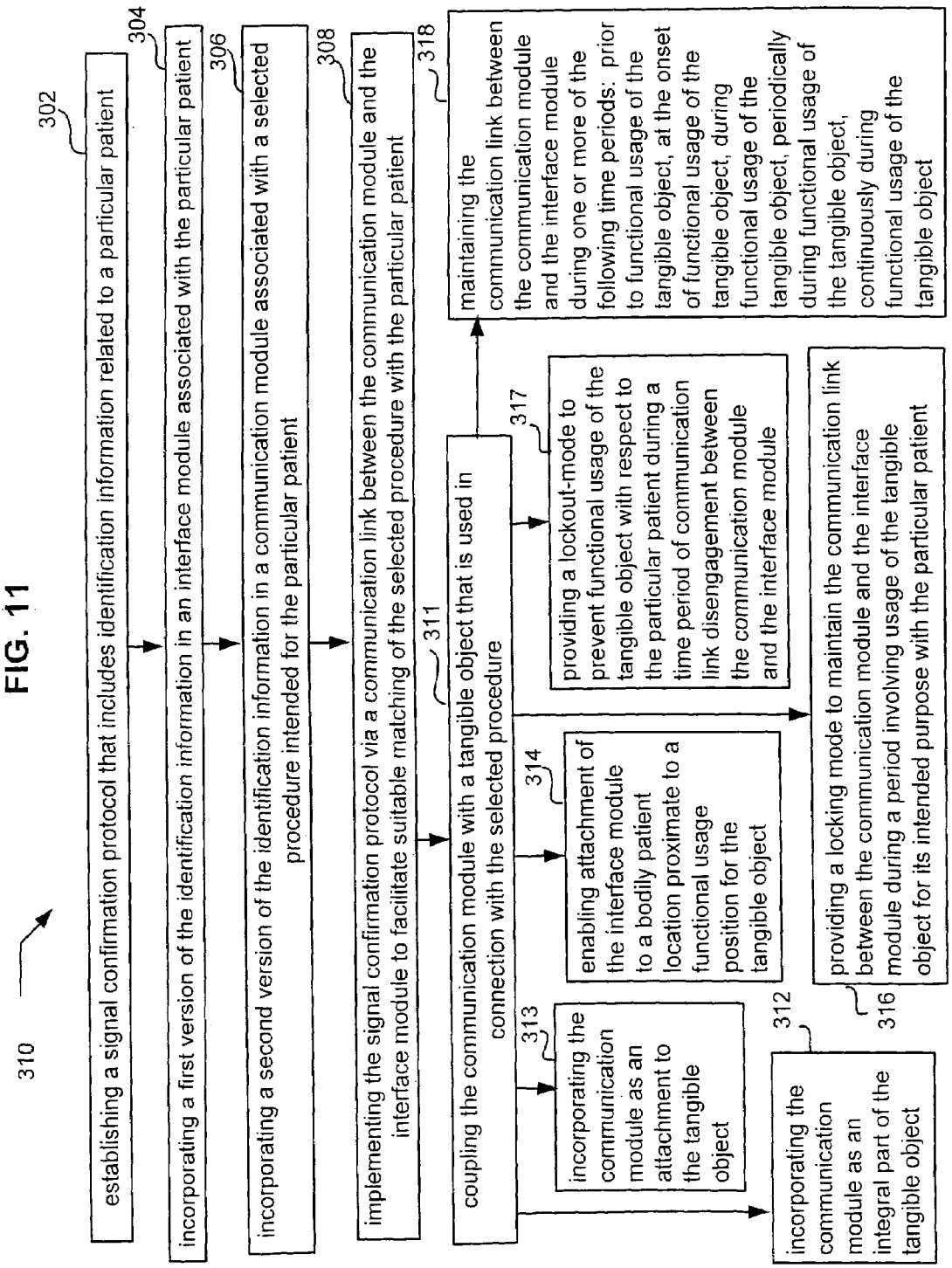
FIGS. 11-14 are flow charts that illustrate more detailed aspects of various exemplary patient verification process implementations.

The exemplary process embodiment features 310 illustrated in FIG. 11 include previously described components 302, 304, 306, 308 in combination with coupling the communication module with a tangible object that is used in connection with the selected procedure (block 311). Additional possible features may include incorporating the communication module as an integral part of the tangible object (block 312), and in some instances may include incorporating the communication module as an attachment to the tangible object (block 313).

Other possible aspects may include enabling attachment of the interface module to a bodily patient location proximate to a functional usage position for the tangible object (block 314), providing a locking mode to maintain the communication link between the communication module and the interface module during a period involving usage of the tangible object for its intended purpose with the particular patient (block 316), and providing a lockout-mode to prevent functional usage of the tangible object with respect to the particular patient during a time period of communication link disengagement between the communication module and the interface module (block 317).

Additional possible features illustrated in FIG. 11 include maintaining the communication link between the communication module and the interface module during one or more of the following time periods: prior to functional usage of the tangible object, at the onset of functional usage of the tangible object, during functional usage of the tangible object, periodically during functional usage of the tangible object, continuously during functional usage of the tangible object (block 318).

Figure 12:
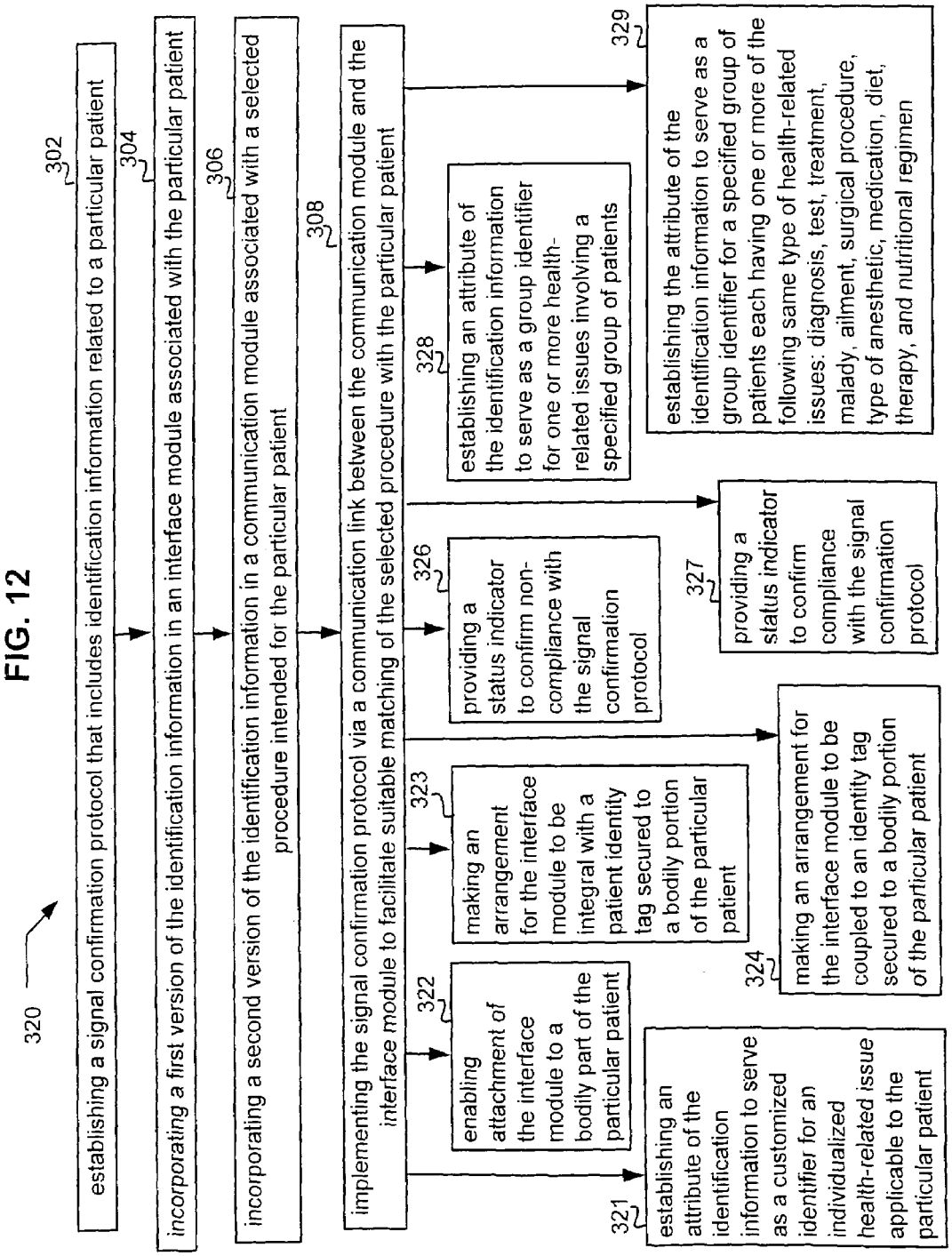

Referring to the illustrated exemplary features 320 of FIG. 12, previously described process components 302, 304, 306, 308 may be combined with other aspects such as establishing an attribute of the identification information to serve as an individualized health-related issue applicable to the particular patient (block 321).

Other possible aspects include enabling attachment of the interface module to a bodily part of the particular patient (block 322), making an arrangement for the interface module to be integral with a patient identity tag secured to a bodily portion of the particular patient (block 323), and making an arrangement for the interface module to be coupled to an identity tag secured to a bodily portion of the particular patient (block 324).

FIG. 12 also illustrates other possible process features including providing a status indicator to confirm compliance (block 327) as well as non-compliance (block 326) with the signal confirmation protocol.

Other possible implementation features may include establishing an attribute of the identification information to serve as a group identifier for one or more health-related issues involving a specified group of patients (block 328), and establishing the attribute of the identification information to serve as a group identifier for a specified group of patients each having one or more of the following same type of health-related issues: diagnosis, test, treatment, malady, ailment, surgical procedure, type of anesthetic, medication, diet, therapy, and nutritional regimen (block 329).

Figure 13:
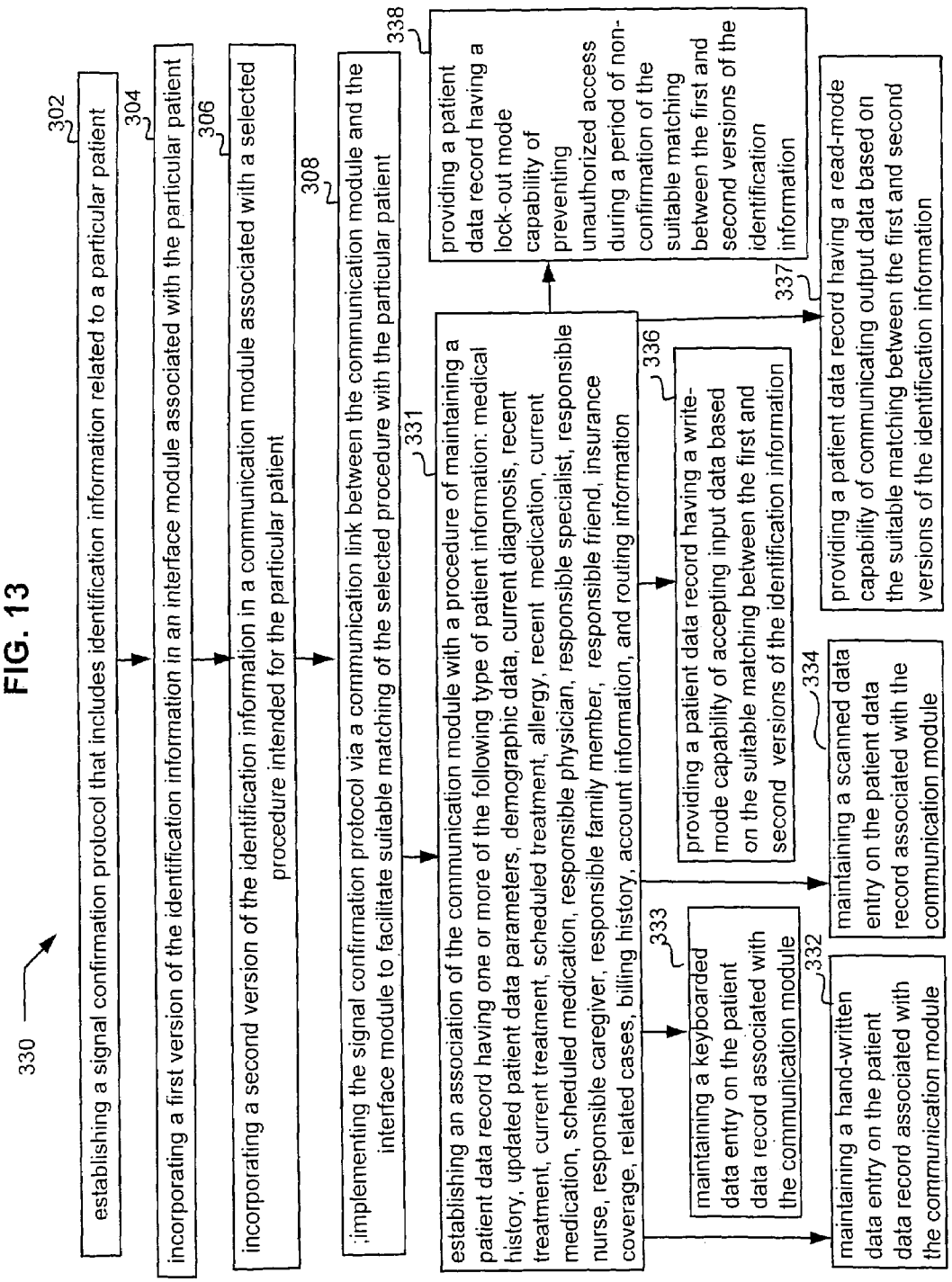

Referring to FIG. 13, various exemplary embodiment features 330 include previously described components 302, 304, 306, 308 along with other possible aspects related to patient data records. For example, some implementations may include establishing an association of the communication module with a procedure of maintaining a patient data record having one or more of the following type of patient information: medical history, updated patient data parameters, demographic data, current diagnosis, recent treatment, current treatment, scheduled treatment, allergy, recent medication, current medication, scheduled medication, responsible physician, responsible specialist, responsible nurse, responsible caregiver, responsible family member, responsible friend, insurance coverage, related cases, billing history, account information, and routing information (block 331).

Other possible aspects include maintaining a hand-written data entry (block 332) or a keyboarded data entry (block 333) or a scanned data entry (block 334) on the patient data record associated with the communication module. Further possible aspects include providing a patient data record having a write-mode capability of accepting input data (block 336) or a read-mode capability of communicating output data (block 336) based on the suitable matching between the first and second versions of the identification information.

Another possible feature includes providing a patient data record having a lock-out mode capability of preventing unauthorized access during a period of non-confirmation of the suitable matching between the first and second versions of the identification information (block 338).

Figure 14:
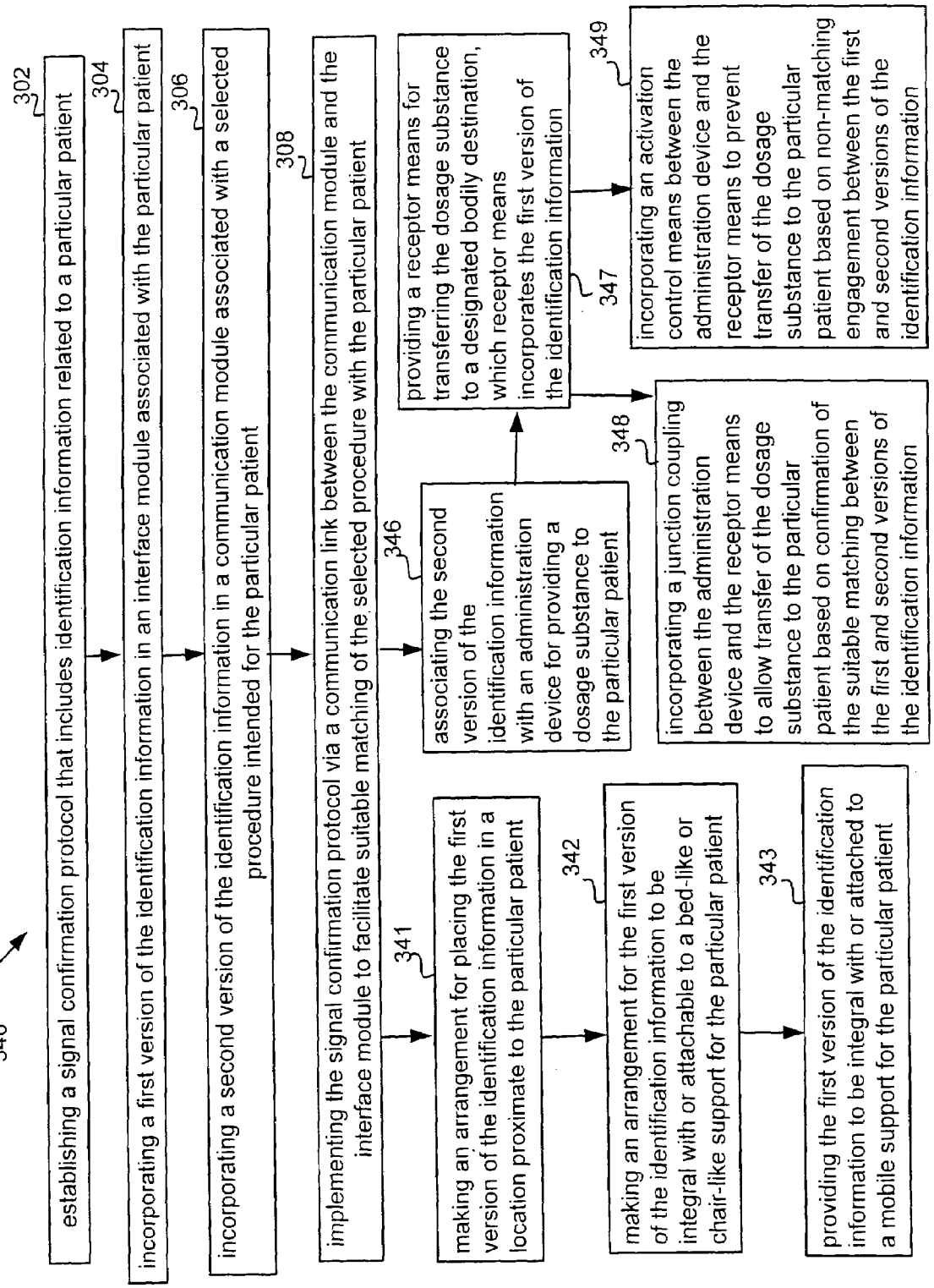

The detailed embodiment features 340 illustrated in FIG. 14 include previous described process components 302, 304, 306, 308 in combination with possible aspects related to various versions of identification information. For example, possible implementation aspects may include making an arrangement for placing a first version of the identification information in a location proximate to the particular patient (block 341), making an arrangement for the first version of the identification information to be integral with or attachable to a bed-like or chair-like support for the particular patient (block 342), and providing the first version of the identification information to be integral with or attached to a mobile support for the particular patient (block 343).

Additional possible features may include associating a second version of the identification information with an administration device for providing a dosage substance to the particular patient (block 346), and providing a receptor means for transferring the dosage substance to a designated bodily destination, which receptor means incorporates the first version of the identification information (block 347).

Other exemplary features may include incorporating a junction coupling between the administration device and the receptor means to allow transfer of the dosage substance to the particular patient based on confirmation of the suitable matching between the first and second versions of the identification information (block 348), and incorporating an activation control means between the administration device and the receptor means to prevent transfer of the dosage substance to the particular patient based on non-matching engagement between the first and second versions of the identification information (block 349).

It will be understood that the signal confirmation protocol may be implemented via various types of communication links (e.g., local link, remote link, wireless link, wired link, conductive link, non-conductive link, etc.), and such communication link may be temporarily or permanently established between an interface module associated with a particular patient and a communication module associated with a selected procedure intended for the particular patient. It will be further understood that such communication links may be dedicated or shared, depending on the circumstances. The exemplary embodiments are disclosed for purposes of illustration only, and are not intended to be limiting.

Figure 15:
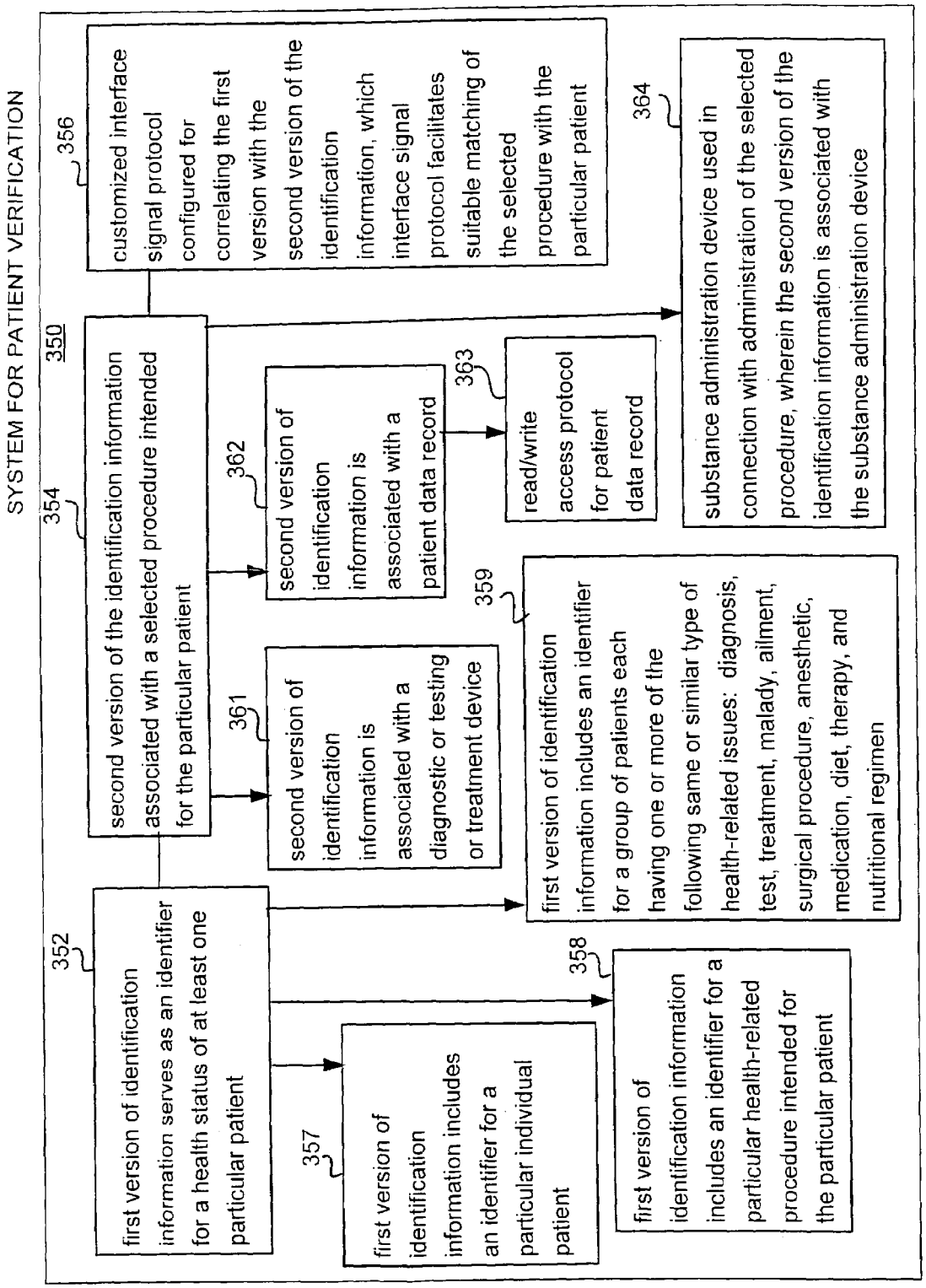
FIG. 15 is a schematic block diagram for a patient verification system.

The schematic block diagram of FIG. 15 illustrates an exemplary system for patient verification 350 that includes a first version of identification information that serves as an identifier for a health status of at least one particular patient (block 352), a second version of the identification information that is associated with a selected procedure intended for the particular patient (block 354); and a customized interface signal protocol configured for correlating the first version with the second version of the identification information, which interface signal protocol facilitates suitable matching of the selected procedure with the particular patient (block 356).

Additional possible system components may provide a first version of identification information that includes an identifier for a particular individual patient (block 357), and in some instances an identifier for a particular health-related procedure intended for the particular patient (block 358). Further possible system components may provide first version of identification information includes an identifier for a group of patients each having one or more of the following same or similar type of health-related issues: diagnosis, test, treatment, malady, ailment, surgical procedure, anesthetic, medication, diet, therapy, and nutritional regimen (block 359).

Other possible system features may provide a second version of identification information associated with a diagnostic or testing or treatment device (block 361), wherein the diagnostic or testing or treatment device may be used in connection with administration of a selected procedure intended for a particular patient. It will be understood that a related implementation features may provide the second version of the identification information as an attachment to or as an integral part of the diagnostic or testing or treatment device.

Further possible system aspects may provide a separate product component not integral with the diagnostic or testing or treatment device, wherein the separate product component includes the second version of the identification information as an attachment to or as an integral part of the diagnostic or testing or treatment device.

Another possible system feature may provide a status indicator that is operably coupled to the first version or the second version of the identification information, wherein the status indicator confirms suitable matching of the selected procedure with the particular patient.

A further possible system feature may provide a control module configured to prevent activation of the diagnostic or testing or treatment device in the event there is an absence of suitable matching of the selected procedure with the particular patient. In some implementations a control module may be configured to allow activation of the diagnostic or testing or treatment device in the event there is confirmation of suitable matching of the selected procedure with the particular patient.

A further possible system feature may provide a second version of identification information associated with a patient data record (block 362), wherein the patient data record may be used in connection with administration of a selected procedure intended for a particular patient. A possible related feature may include a read/write access protocol (block 363) for the patient data record.

Other related system features regarding a patient data record may include the second version of the identification information as an attachment to or as an integral part of the patient data record. A further system aspect may provide a separate product component not integral with the patient data record, wherein the separate product component includes the second version of the identification information as an attachment to or as an integral part of the patient data record.

Further system aspects may include a status indicator that is operably coupled to the first version or the second version of the identification information, wherein the status indicator confirms the suitable matching of the patient data record with the particular patient. Some implementation may include a control module configured to prevent activation of the patient data record in the event there is an absence of suitable matching of the patient data record with the particular patient. An additional possible implementation feature may include a control module configured to allow activation of the patient data record in the event there is confirmation of suitable matching of the selected procedure with the particular patient.

Additional aspects related to patient data records may include an access protocol to prevent read access to the patient data record in the event there is an absence of suitable matching of the selected procedure with the particular patient. Such an access protocol may in some instances prevent write access to the patient data record in the event there is an absence of suitable matching of the selected procedure with the particular patient.

Other possible implementation features may include an access protocol configured to allow read access to the patient data record in the event there is confirmation of suitable matching of the selected procedure with the particular patient. In some instances the access protocol may be configured to allow write access to the patient data record in the event there is correlation between the first and second versions of the identification information.

It will be understood that an exemplary access protocol may allow one or more of the following type of input write access to the patient data record in the event there is correlation between the first and second versions of the identification information: handwritten, keyboarded, scanned, oral, faxed, remote transmittal, wireless transmittal, data modification, data deletion, hyperlinked data entry, and cross-reference link.

Some exemplary embodiments may include an access protocol that provides one or more of the following type of output read access to the patient data record: hardcopy view, hardcopy printout, display monitor, remote access, text access, audio access, image access, fax access, hyperlinked access, and cross-reference link.

FIG. 15 shows another possible system aspect that provides a first version of identification information including an identifier for a group of patients each having one or more of the following same or similar type of health-related issues: diagnosis, test, treatment, malady, ailment, surgical procedure, anesthetic, medication, diet, therapy, and nutritional regimen (block 359).

A further possible system aspect may include a substance administration device used in connection with administration of the selected procedure, wherein a second version of identification information is associated with the substance administration device (block 364). It will be understood that additional system aspects related to a substance administration device may provide a second version of the identification information as an integral part of the substance administration device. Some implementations may include a separate product component not integral with the substance administration device, wherein the separate product component includes the second version of the identification information as an integral part.

Additional possible system features may include a status indicator that is operably coupled to a first version or a second version of the identification information, wherein the status indicator confirms the correlation between the first and second versions of the identification information.

Some exemplary system embodiments may include a control module operably coupled with the substance administration device to prevent activation of the substance administration device in the event there is an absence of correlation between first and second versions of the identification information. In some instances a control module may be operably coupled with the substance administration device to allow activation of the substance administration device in the event there is confirmation of correlation between first and second versions of the identification information.

Figure 16:
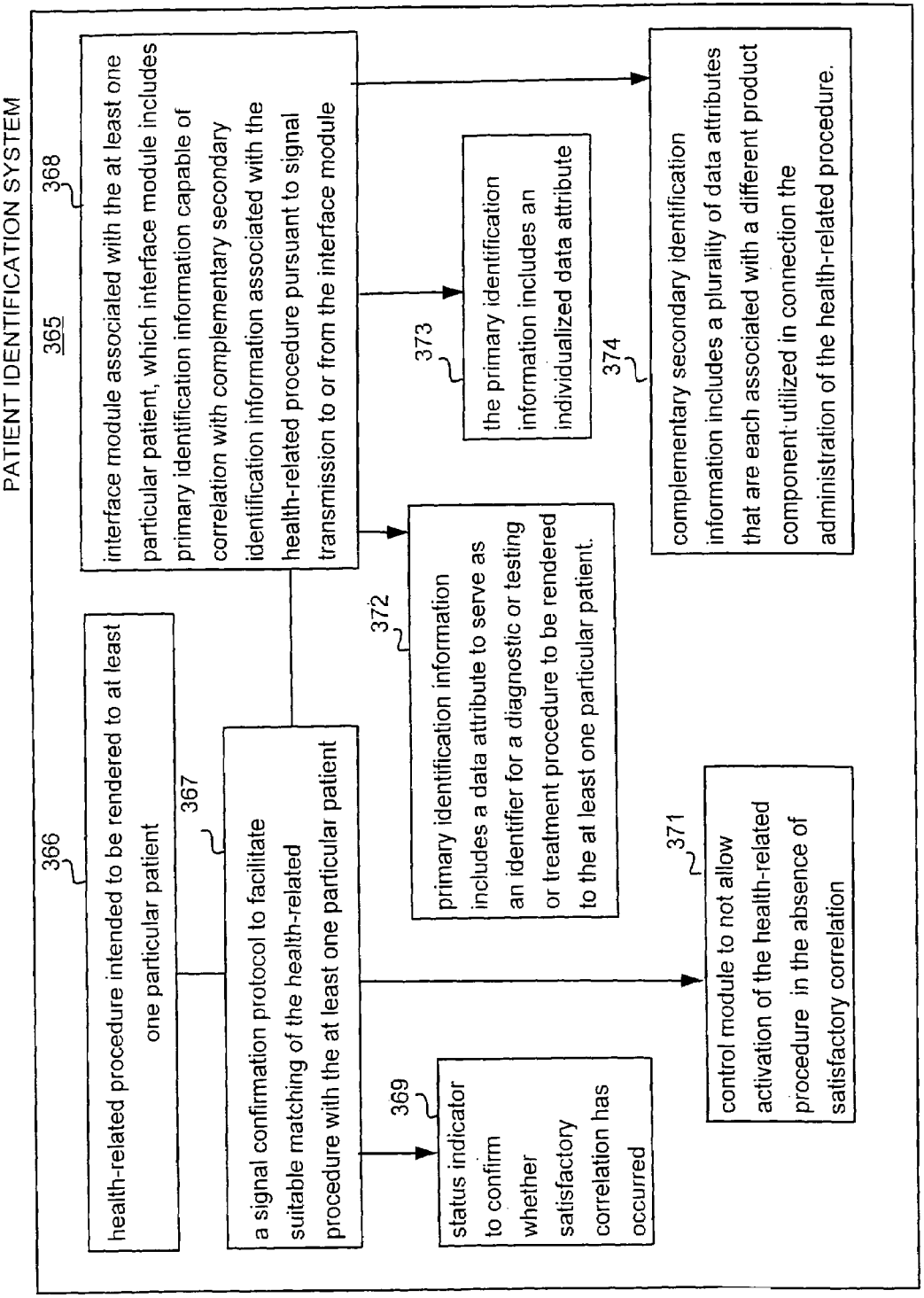
FIGS. 16-19 schematically illustrate additional patient identification system embodiments.

The exemplary patient identification system embodiment 365 of FIG. 16 includes a health-related procedure that is intended to be rendered to at least one particular patient (block 366); a signal confirmation protocol to facilitate suitable matching of the health-related procedure with the at least one particular patient (block 367); and an interface module associated with the at least one particular patient, which interface module includes primary identification information capable of correlation with complementary secondary identification information associated with the health-related procedure pursuant to signal transmission to or from the interface module (block 368).

Further system aspects may include a status indicator to confirm whether satisfactory correlation has occurred (block 369) between a particular patient and a health-related procedure. In some instances an exemplary control module may be configured to not allow activation of the health-related procedure in the absence of satisfactory correlation (block 371).

Another system aspect may provide primary identification information that includes a data attribute to serve as an identifier for a diagnostic or testing or treatment procedure to be rendered to at least one particular patient (block 372).

Additional possible system aspects may provide primary identification information including an individualized data attribute (block 373) that may serve as a customized identifier for at least one particular patient. A further exemplary system aspect may provide complementary secondary identification information including a plurality of data attributes that are each associated with a different product component utilized in connection with the administration of the health-related procedure (block 374).

Figure 17:
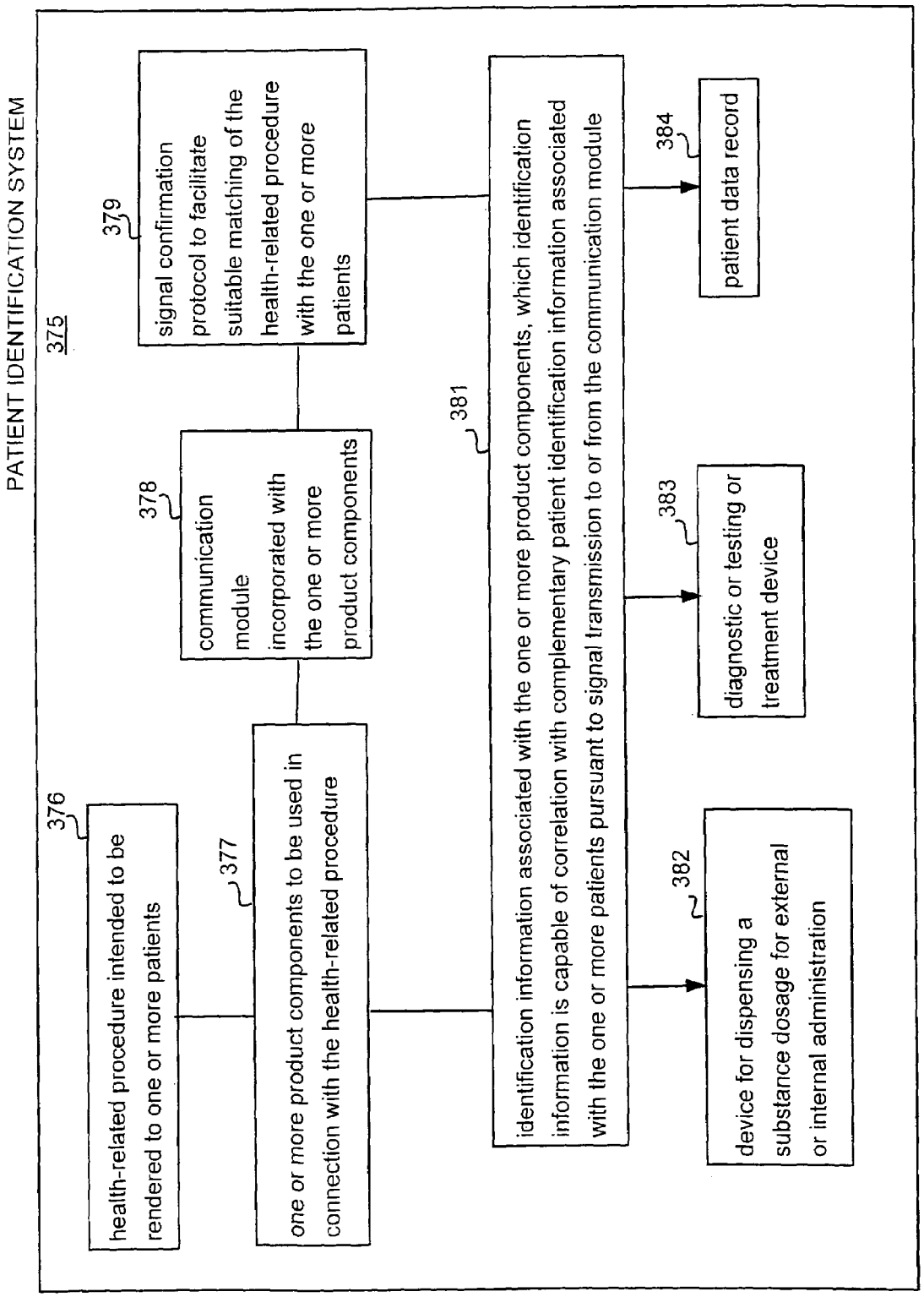

Referring to the schematic diagram of FIG. 17, an exemplary patient identification system embodiment 375 may include a health-related procedure that is intended to be rendered to one or more patients (block 376); one or more product components to be used in connection with the health-related procedure (block 377); a communication module incorporated with the one or more product components (block 378); a signal confirmation protocol to facilitate suitable matching of the health-related procedure with the one or more patients (block 379); and identification information associated with the one or more product components, which identification information is capable of correlation with complementary patient identification information associated with the one or more patients pursuant to signal transmission to or from the communication module (block 381).

It will be understood that additional system components such as a status indicator may be operably coupled with identification information to confirm compliance with a signal confirmation protocol for establishing suitable matching of a health-related procedure with one or more patients.

It will be further understood that a control module may be configured to either allow or prevent activation of a health-related procedure base on a determination of suitable matching of a health-related procedure with one or more patients.

Other possible system aspects may provide various product components associated with patient identification information. For example such product components may include a device for dispensing a substance dosage for external or internal administration to the particular patient (block 382), a diagnostic or testing or treatment device (block 383), and a patient data record (block 384).

Figure 18:
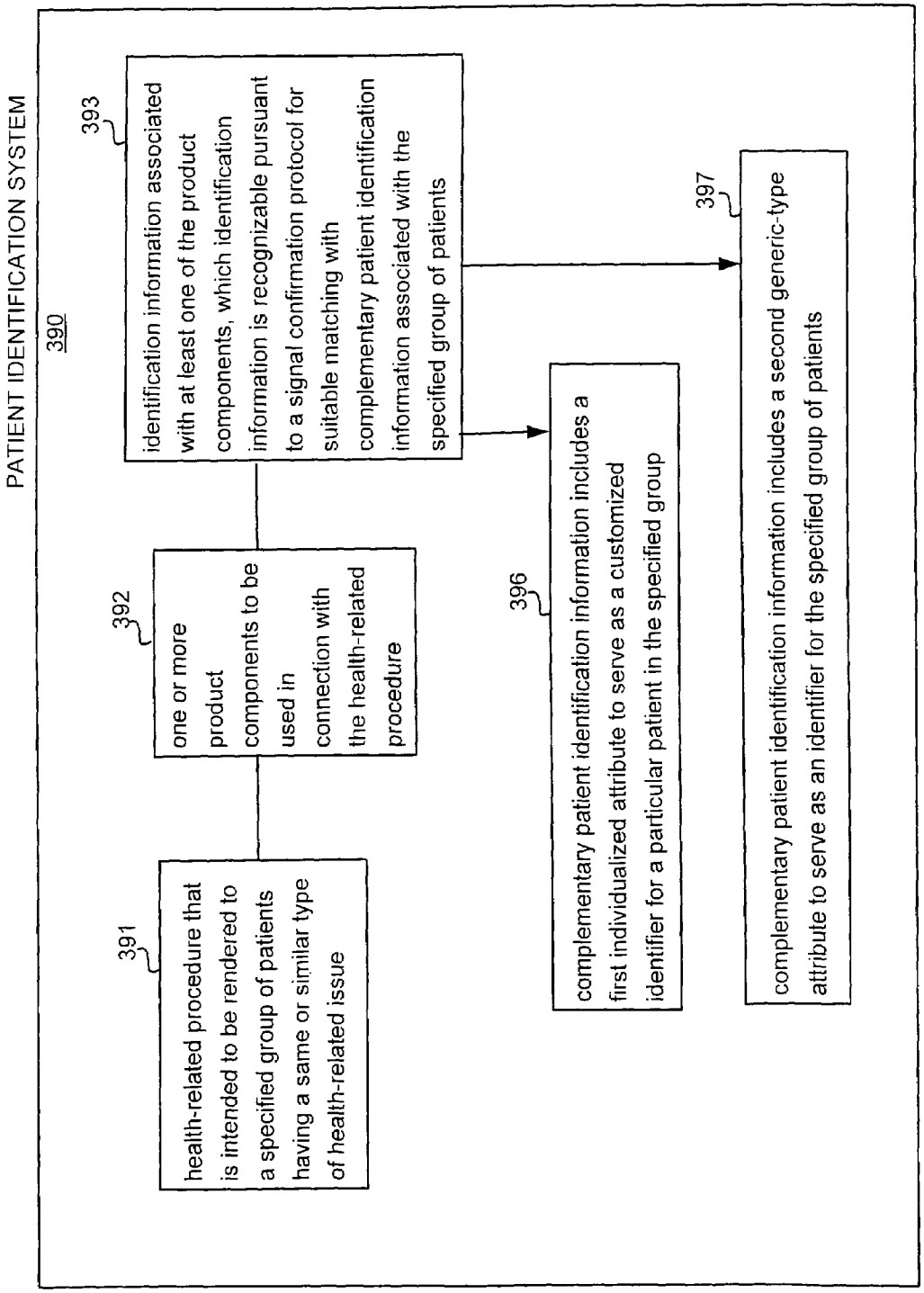

Referring to the schematic diagram of FIG. 18, an exemplary patient identification system embodiment 390 may include a health-related procedure that is intended to be rendered to a specified group of patients having a same or similar type of health-related issue (block 391); one or more product components to be used in connection with the health-related procedure (block 392); and identification information associated with at least one of the product components, which identification information is recognizable pursuant to a signal confirmation protocol for suitable matching with complementary patient identification information associated with the specified group of patients (block 393). It will be understood that such complementary patient identification may include an attribute to serve as an identifier for a diagnostic or testing or treatment procedure.

Additional possible system aspects may provide complementary patient identification information that includes a first individualized attribute to serve as a customized identifier for a particular patient in the specified group (block 396), and that may include a second generic-type attribute to serve as an identifier for the specified group of patients (block 397).

Figure 19:
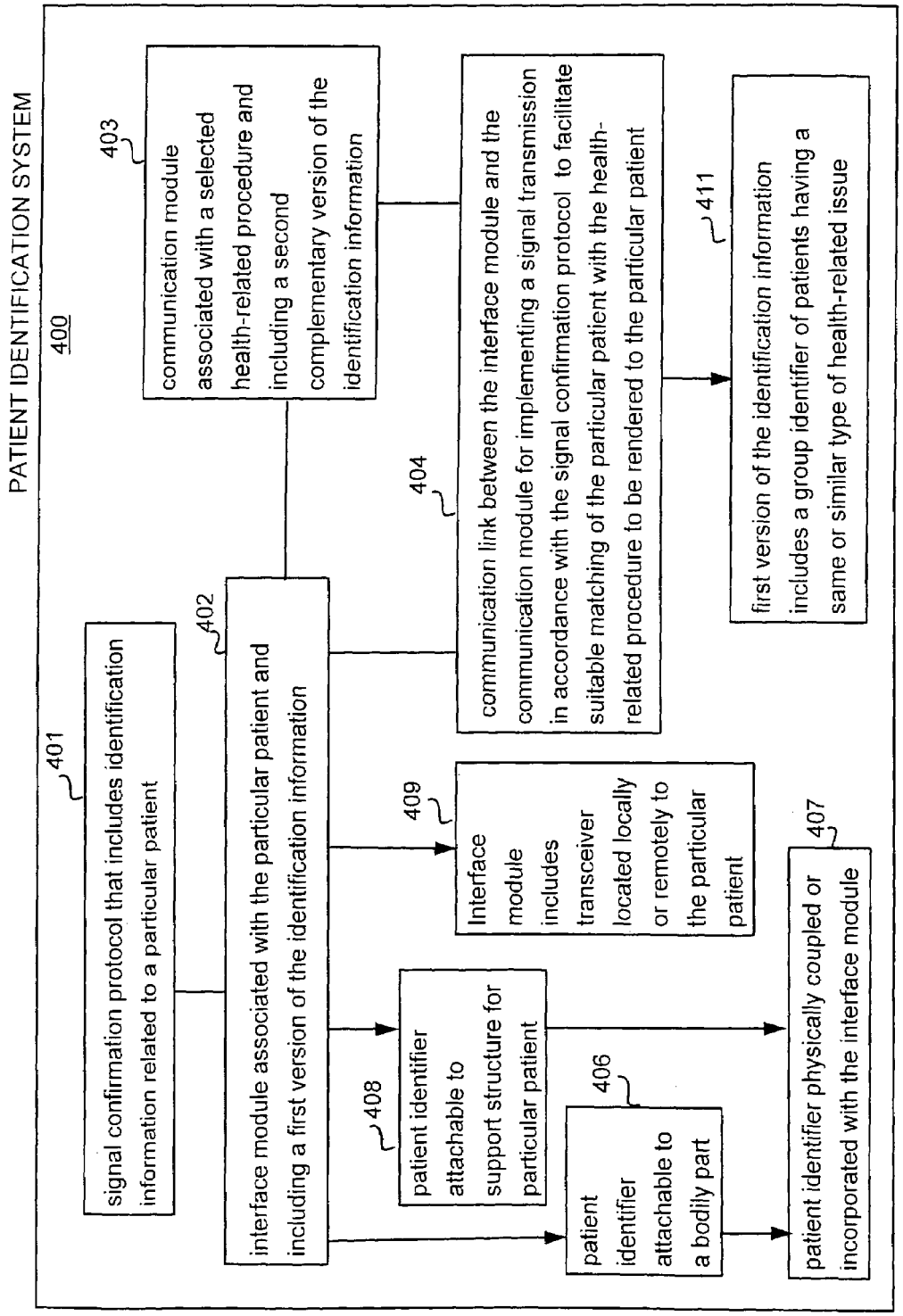

A further exemplary system embodiment 400 for patient identification shown in FIG. 19 provides a signal confirmation protocol that includes identification information related to a particular patient (block 401); an interface module associated with the particular patient and including a first version of the identification information (block 402); and a communication module associated with a selected health-related procedure and that includes a second complementary version of the identification information (block 403). An additional possible component includes a communication link between the interface module and the communication module for implementing a signal transmission in accordance with the signal confirmation protocol to facilitate suitable matching of the particular patient with the health-related procedure to be rendered to the particular patient (block 404).

Other possible implementation features may provide a first version of identification information that includes an individual identifier for a particular patient. A system implementation may include a computer program product having instructions encoded on storage or transmission media, which instructions implement a process for verification of correlation between the first version of the identification information associated with the particular patient and the second version of the identification information associated with a health-related procedure to be rendered to the particular patient.

Various types of additional system aspects that may be provided are shown in FIG. 19. For example, an exemplary system embodiment may provide patient identifier components that are physically coupled or incorporated with an interface module (block 407). A possible patient identifier may be attachable to a bodily part (block 406), and a possible patient identifier may be attachable to support structure for a particular patient (block 408).

Some system implementations may provide an interface module that includes a transceiver located locally (e.g., in proximity to the particular patient) or remotely to the particular patient (block 409). Another possible system implementation may provide a first version of the identification information that includes a group identifier of patients having a same or similar type of health-related issue (block 411).

Figure 20:
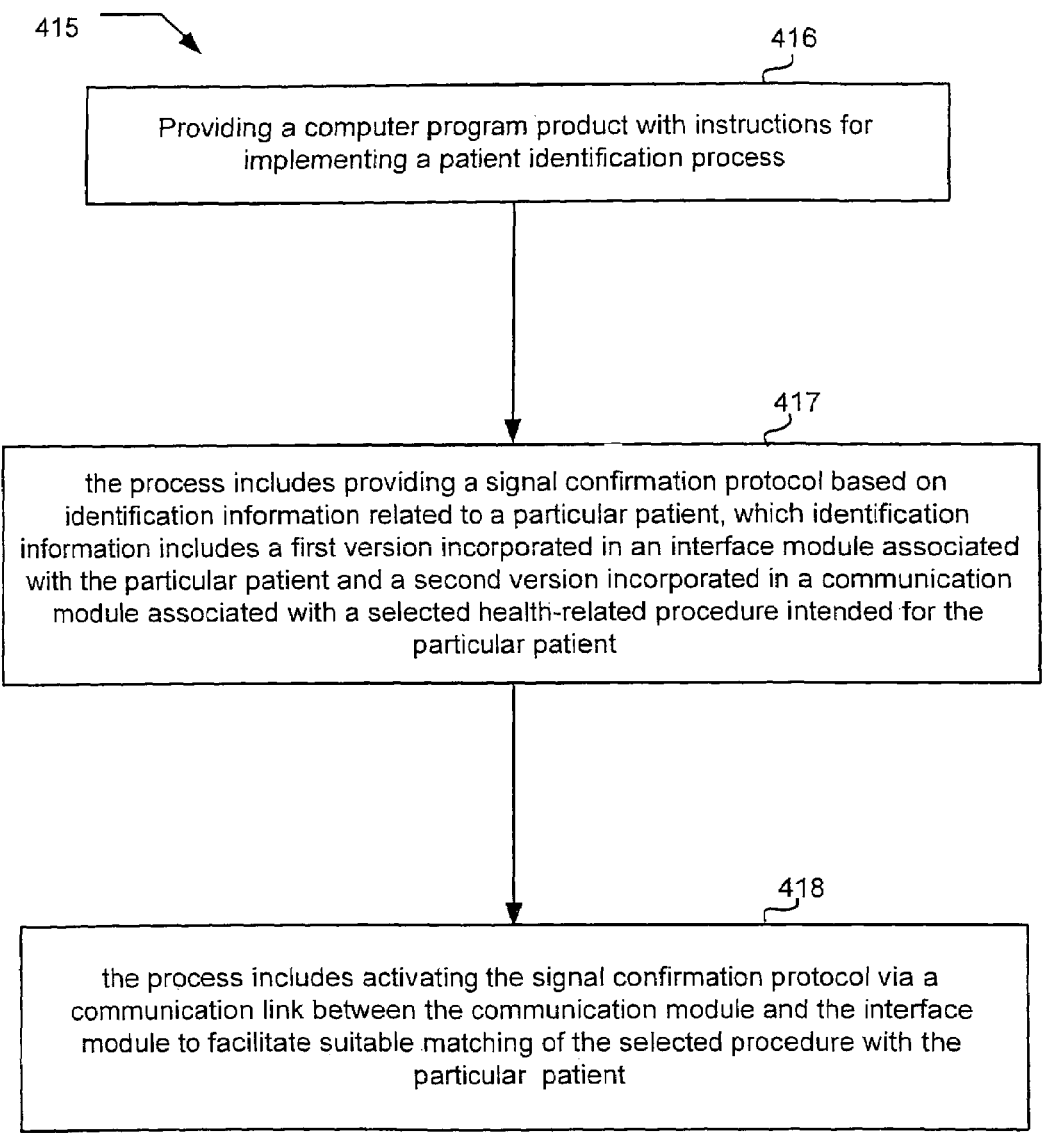
FIG. 20 shows an exemplary computer program product for encoding an exemplary process embodiment.

It will be understood that various process components may be incorporated in a computer program product 415 as shown in FIG. 20. For example, some embodiments may provide a computer program product having instructions for implementing a patient identification process (block 416), wherein the process may provide a signal confirmation protocol based on identification information related to a particular patient, which identification information includes a first version incorporated in an interface module associated with the particular patient and a second version incorporated in a communication module associated with a selected health-related procedure intended for the particular patient (block 417). The exemplary process may further activate the signal confirmation protocol via a communication link between the communication module and the interface module to facilitate suitable matching of the selected procedure with the particular patient (block 418).

Other exemplary computer program product features may be incorporated in a process embodiment that allowing activation of the selected health-related procedure in the event the signal confirmation protocol establishes satisfactory correlation between the first and second versions of the identification information. A related exemplary computer program product features may be incorporated in a process embodiment that prevents activation of the selected health-related procedure in the event the signal confirmation protocol fails to establish satisfactory correlation between the first and second versions of the identification information.

It will be understood by those skilled in the art that the various components and elements disclosed in the block diagrams herein as well as the various steps and sub-steps disclosed in the flow charts herein may be incorporated together in different claimed combinations in order to enhance possible benefits and advantages.

It is to be further understood that various aspects of the methods and processes disclosed in FIGS. 4-8 and FIGS. 10-14 can be incorporated in one or more different types of computer program products with a carrier medium having program instructions encoded thereon. Some exemplary computer program products may be implemented in storage carrier media having program instructions encoded thereon. In some instances exemplary computer program products may be implemented in communication signal carrier media having program instructions encoded thereon.

The exemplary system, apparatus, and computer program product embodiments disclosed herein including FIGS. 1-3 and FIG. 9 and FIGS. 15-19 along with other components, devices, know-how, skill and techniques that are known in the art have the capability of implementing and practicing the methods and processes shown in FIGS. 4-8 and FIGS. 10-14 and FIG. 20. However it is to be further understood by those skilled in the art that other systems, apparatus and technology may be used to implement and practice such methods and processes. Those skilled in the art will also recognize that the various aspects of the embodiments for methods, processes, products, and systems as described herein can be implemented individually and/or collectively by a wide range of hardware, software, firmware, or any combination thereof.

Exemplary embodiments disclosed herein provide a verification technique that facilitates administration of a health-related procedure to an intended recipient patient or group of patients. An interface template or signal protocol may be configured to establish suitable matching between the patient and various types of objects used to administer the health-related procedure.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost versus efficiency tradeoffs. Those having skill in the art will appreciate that there are various vehicles by which processes and/or systems and/or other technologies described herein can be effected (e.g., hardware, software, and/or firmware), and that the preferred vehicle may vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle may be deployed and the specific concerns (e.g., speed, flexibility, or predictability) of the implementer, any of which may vary. Those skilled in the art will recognize that optical aspects of implementations will require optically-oriented hardware, software, and or firmware.

The foregoing detailed description has set forth various embodiments of the devices and/or processes via the use of block diagrams, flow diagrams, operation diagrams, flowcharts, illustrations, and/or examples. Insofar as such block diagrams, operation diagrams, flowcharts, illustrations, and/or examples contain one or more functions and/or operations, it will be understood by those within the art that each function and/or operation within such block diagrams, operation diagrams, flowcharts, illustrations, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, and computer memory; and transmission type media such as digital and analog communication links using TDM or IP based communication links (e.g., packet links).

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

The herein described aspects depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality. Any two components capable of being so associated can also be viewed as being "operably couplable" to each other to achieve the desired functionality. Specific examples of operably couplable include but are not limited to physically mateable and/or physically interacting components and/or wirelessly interactable and/or wirelessly interacting components.

As a further definition of "open" terms in the present specification and claims, it will be understood that usage of a language construction "A or B" is generally interpreted as a non-exclusive "open term" meaning: A alone, B alone, A and B together.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A system comprising:
    circuitry configured to confirm physical engagement involving at least one communication module and at least one interface module that at least includes one or more surface shape attributes that serve as at least one of (i) a procedure identifier or (ii) a group identifier for at least one of a diagnosis, a test, a treatment, a malady, an ailment, a surgical procedure, an anesthetic, a medication, a diet, a therapy, or a nutritional regimen;
    circuitry configured to activate one or more product components associated with at least one health-related procedure at least partly in response to confirmation of physical engagement involving the at least one communication module and the at least one interface module; and
    circuitry configured to access at least one portion of at least one patient data record of at least one individual identified based at least partly on identification information associated with the at least one interface module, at least partly in response to confirmation of physical engagement involving the at least one communication module and the at least one interface module.

2. The system of claim 1, wherein the circuitry configured to confirm physical engagement involving at least one communication module and at least one interface module that at least includes one or more surface shape attributes that serve as at least one of a procedure identifier or a group identifier comprises:
    circuitry configured to confirm physical complementary matching engagement involving at least one communication module and at least one interface module that at least includes one or more surface shape attributes that serve as at least one of a procedure identifier or a group identifier.

3. The system of claim 1, wherein the circuitry configured to confirm physical engagement involving at least one communication module and at least one interface module that at least includes one or more surface shape attributes that serve as at least one of a procedure identifier or a group identifier comprises:
    circuitry configured to confirm physical engagement involving at least one communication module and at least one interface module that at least includes one or more of the following types of surface shape attributes that serve as at least one of a procedure identifier or a group identifier: pattern, projection, recess, matrix, and/or contour.

4. The system of claim 1, wherein the circuitry configured to confirm physical engagement involving at least one communication module and at least one interface module that at least includes one or more surface shape attributes that serve as at least one of a procedure identifier or a group identifier comprises:
    circuitry configured to confirm physical engagement involving at least one communication module and at least one interface module that at least includes one or more geometric shapes that serve as at least one of a procedure identifier or a group identifier.

5. The system of claim 1, wherein the circuitry configured to confirm physical engagement involving at least one communication module and at least one interface module that at least includes one or more surface shape attributes that serve as at least one of a procedure identifier or a group identifier comprises:
    circuitry configured to confirm physical engagement involving at least one communication module and at least one interface module that at least includes one or more surface shape attributes that serve as an identifier for one or more procedures involving a specified test and/or treatment.

6. The system of claim 1, wherein the circuitry configured to confirm physical engagement involving at least one communication module and at least one interface module that at least includes one or more surface shape attributes that serve as at least one of a procedure identifier or a group identifier comprises:
    circuitry configured to confirm physical engagement involving at least one communication module and at least one interface module that at least includes (i) one or more surface shape attributes that serve as a procedure identifier and (ii) one or more surface shape attributes that serve as a group identifier.

7. The system of claim 1, wherein the circuitry configured to confirm physical engagement involving at least one communication module and at least one interface module that at least includes one or more surface shape attributes that serve as at least one of a procedure identifier or a group identifier comprises:
    circuitry configured to confirm, based on one or more conductive contacts, physical engagement involving at least one communication module and at least one interface module that at least includes one or more surface shape attributes that serve as at least one of a procedure identifier or a group identifier.

8. The system of claim 1, wherein the circuitry configured to activate one or more product components associated with at least one health-related procedure at least partly in response to confirmation of physical engagement involving the at least one communication module and the at least one interface module comprises:
   circuitry configured to activate one or more product components associated with at least one health-related procedure based at least partly on at least one signal confirmation protocol.

9. The system of claim 1, wherein the circuitry configured to activate one or more product components associated with at least one health-related procedure at least partly in response to confirmation of physical engagement involving the at least one communication module and the at least one interface module comprises:
   circuitry configured to activate one or more product components associated with at least one health-related procedure based at least partly on information received from the at least one interface module, at least partly in response to confirmation of physical engagement involving the at least one communication module and the at least one interface module.

10. The system of claim 1, wherein the circuitry configured to activate one or more product components associated with at least one health-related procedure at least partly in response to confirmation of physical engagement involving the at least one communication module and the at least one interface module comprises:
    circuitry configured to activate at least one of a testing, treatment, dispenser, and/or diagnostic device associated with at least one health-related procedure at least partly in response to confirmation of physical engagement involving the at least one communication module and the at least one interface module.

11. The system of claim 1, wherein the circuitry configured to access at least one portion of at least one patient data record of at least one individual identified based at least partly on identification information associated with the at least one interface module, at least partly in response to confirmation of physical engagement involving the at least one communication module and the at least one interface module comprises:
    circuitry configured to write data to at least one portion of at least one patient data record of at least one individual identified based at least partly on identification information associated with the at least one interface module, at least partly in response to confirmation of physical engagement involving the at least one communication module and the at least one interface module.

12. The system of claim 1, wherein the circuitry configured to access at least one portion of at least one patient data record of at least one individual identified based at least partly on identification information associated with the at least one interface module, at least partly in response to confirmation of physical engagement involving the at least one communication module and the at least one interface module comprises:
    circuitry configured to read data from at least one portion of at least one patient data record of at least one individual identified based at least partly on identification information associated with the at least one interface module, at least partly in response to confirmation of physical engagement involving the at least one communication module and the at least one interface module.

13. The system of claim 1, wherein the circuitry configured to access at least one portion of at least one patient data record of at least one individual identified based at least partly on identification information associated with the at least one interface module, at least partly in response to confirmation of physical engagement involving the at least one communication module and the at least one interface module comprises:
    circuitry configured to display at least one portion of at least one patient data record of at least one individual identified based at least partly on identification information associated with the at least one interface module, at least partly in response to confirmation of physical engagement involving the at least one communication module and the at least one interface module.

14. The system of claim 1, wherein the circuitry configured to access at least one portion of at least one patient data record of at least one individual identified based at least partly on identification information associated with the at least one interface module, at least partly in response to confirmation of physical engagement involving the at least one communication module and the at least one interface module comprises:
    circuitry configured to access at least one portion of at least one patient data record of at least one individual identified based at least partly on at least one signal confirmation protocol.

15. The system of claim 1, wherein the circuitry configured to access at least one portion of at least one patient data record of at least one individual identified based at least partly on identification information associated with the at least one interface module, at least partly in response to confirmation of physical engagement involving the at least one communication module and the at least one interface module comprises:
    circuitry configured to access at least one portion of at least one patient data record of at least one individual identified based at least partly on identification information received from the at least one interface module, at least partly in response to confirmation of physical engagement involving the at least one communication module and the at least one interface module.

16. The system of claim 1, wherein the circuitry configured to access at least one portion of at least one patient data record of at least one individual identified based at least partly on identification information associated with the at least one interface module, at least partly in response to confirmation of physical engagement involving the at least one communication module and the at least one interface module comprises:
    circuitry configured to access at least one portion of at least one remote patient data record of at least one individual identified based at least partly on identification information associated with the at least one interface module, at least partly in response to confirmation of physical engagement involving the at least one communication module and the at least one interface module.

17. The system of claim 1, wherein the circuitry configured to access at least one portion of at least one patient data record of at least one individual identified based at least partly on identification information associated with the at least one interface module, at least partly in response to confirmation of physical engagement involving the at least one communication module and the at least one interface module comprises:
    circuitry configured to access one or more of the following types of information from at least one patient data record of at least one individual identified based at least partly on identification information associated with the at least one interface module, at least partly in response to confirmation of physical engagement involving the at least one communication module and the at least one interface module: medical history, demographic, diagnosis, treatment, allergy, medication, physician, specialist, nurse, caregiver, family member, friend, insurance coverage, related case, billing, account, and/or routing.

18. A method at least partly implemented using one or more processing components, the method comprising:

confirming physical engagement involving at least one communication module and at least one interface module that at least includes one or more surface shape attributes that serve as at least one of (i) a procedure identifier or (ii) a group identifier for at least one of a diagnosis, a test, a treatment, a malady, an ailment, a surgical procedure, an anesthetic, a medication, a diet, a therapy, or a nutritional regimen;

activating one or more product components associated with at least one health-related procedure at least partly in response to confirming physical engagement involving the at least one communication module and the at least one interface module; and accessing at least one portion of at least one patient data record of at least one individual identified based at least partly on identification information associated with the at least one interface module, at least partly in response to confirming physical engagement involving the at least one communication module and the at least one interface module.

19. A computer program product comprising:

one or more non-transitory media including at least:

one or more instructions for confirming physical engagement involving at least one communication module and at least one interface module that at least includes one or more surface shape attributes that serve as at least one of (i) a procedure identifier or (ii) a group identifier for at least one of a diagnosis, a test, a treatment, a malady, an ailment, a surgical procedure, an anesthetic, a medication, a diet, a therapy, or a nutritional regimen;

one or more instructions for activating one or more product components associated with at least one health-related procedure at least partly in response to confirmation of physical engagement involving the at least one communication module and the at least one interface module; and one or more instructions for accessing at least one portion of at least one patient data record of at least one individual identified based at least partly on identification information associated with the at least one interface module, at least partly in response to confirmation of physical engagement involving the at least one communication module and the at least one interface module.

* * * * *